US007153501B2

(12) United States Patent
Friedlander et al.

(10) Patent No.: US 7,153,501 B2
(45) Date of Patent: Dec. 26, 2006

(54) HEMATOPOIETIC STEM CELLS AND METHODS OF TREATMENT OF NEOVASCULAR EYE DISEASES THEREWITH

(75) Inventors: Martin Friedlander, Del Mar, CA (US); Atsushi Otani, San Diego, CA (US); Karen Da Silva, Irvine, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/628,783

(22) Filed: Jul. 25, 2003

(65) Prior Publication Data

US 2004/0197902 A1 Oct. 7, 2004

Related U.S. Application Data

(60) Provisional application No. 60/467,051, filed on May 2, 2003, provisional application No. 60/398,522, filed on Jul. 25, 2002.

(51) Int. Cl.

| | |
|---|---|
| ***A61K 48/00*** | (2006.01) |
| ***C12N 15/63*** | (2006.01) |
| *A01N 65/00* | (2006.01) |
| *C12N 5/08* | (2006.01) |

(52) U.S. Cl. ................. 424/93.21; 435/455; 435/320.1

(58) Field of Classification Search ............. 424/93.21; 435/455, 325, 320.1; 536/23.5

See application file for complete search history.

(56) References Cited

U.S. PATENT DOCUMENTS

| | | | | |
|---|---|---|---|---|
| 6,767,727 | B1 * | 7/2004 | Glucksmann et al. | 435/196 |
| 2003/0017564 | A1 * | 1/2003 | Schimmel et al. | 435/184 |

OTHER PUBLICATIONS

Smith, L.E.H. Stem cells go for the eyes. Nature Medicine 8:932, 2002.*

Otani et al. Bone marrow-derived stem cells target retinal astrocytes and can promote or inhibit retinal angiogenesis. Nature Medicine 8:1004-1010, 2002.*

McFarland et al. Gene therapy for proliferative ocular diseases. Expert Opin. Biol. Ther. 4: 1053-1058, 2004.*

* cited by examiner

*Primary Examiner*—Quang Nguyen
(74) *Attorney, Agent, or Firm*—Olson & Hierl, Ltd.

(57) ABSTRACT

Isolated, mammalian, bone marrow-derived, lineage negative hematopoietic stem cell populations ($Lin^-$ HSC) contain endothelial progenitor cells (EPC) capable of forming retinal blood vessels. At least about 50% of the cells in the isolated $Lin^-$ HSC population include cell surface markers for CD31 and c-kit. Up to about 8% of the cells can include the Sca-1 cell marker, and up to about 4% of the cells can include the Flk-1/KDR marker. The isolated $Lin^-$ HSC populations of the present invention are useful for treatment of ocular vascular diseases. The isolated $Lin^-$ HSC populations that have been transfected with therapeutically useful genes are also provided, which are useful for delivering genes to the eye for cell-based gene therapy.

3 Claims, 17 Drawing Sheets

C

DNA encoding His-tagged T2 fragment of human TrpRS

```
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg agacaataac cctgataaat gcttcaataa tattgaaaaa ggaagagtat 600
gagtattcaa catttccgtg tcgcccttat tccctttttt gcggcatttt gccttcctgt 660
ttttgctcac ccagaaacgc tggtgaaagt aaaagatgct gaagatcagt tgggtgcacg 720
agtgggttac atcgaactgg atctcaacag cggtaagatc cttgagagtt ttcgccccga 780
agaacgtttt ccaatgatga gcacttttaa agttctgcta tgtggcgcgg tattatcccg 840
tattgacgcc gggcaagagc aactcggtcg ccgcatacac tattctcaga atgacttggt 900
tgagtactca ccagtcacag aaaagcatct tacggatggc atgacagtaa gagaattatg 960
cagtgctgcc ataaccatga gtgataacac tgcggccaac ttacttctga caacgatcgg 1020
aggaccgaag gagctaaccg cttttttgca caacatgggg gatcatgtaa ctcgccttga 1080
tcgttgggaa ccggagctga atgaagccat accaaacgac gagcgtgaca ccacgatgcc 1140
tgcagcaatg gcaacaacgt tgcgcaaact attaactggc gaactactta ctctagcttc 1200
ccggcaacaa ttaatagact ggatggaggc ggataaagtt gcaggaccac ttctgcgctc 1260
ggcccttccg gctggctggt ttattgctga taaatctgga gccggtgagc gtgggtctcg 1320
cggtatcatt gcagcactgg ggccagatgg taagccctcc cgtatcgtag ttatctacac 1380
gacggggagt caggcaacta tggatgaacg aaatagacag atcgctgaga taggtgcctc 1440
actgattaag cattggtaac tgtcagacca agtttactca tatatacttt agattgattt 1500
aaaacttcat ttttaattta aaaggatcta ggtgaagatc ctttttgata atctcatgac 1560
caaaatccct taacgtgagt tttcgttcca ctgagcgtca gaccccgtag aaaagatcaa 1620
aggatcttct tgagatcctt tttttctgcg cgtaatctgc tgcttgcaaa caaaaaaacc 1680
accgctacca gcggtggttt gtttgccgga tcaagagcta ccaactcttt ttccgaaggt 1740
aactggcttc agcagagcgc agataccaaa tactgtcctt ctagtgtagc cgtagttagg 1800
ccaccacttc aagaactctg tagcaccgcc tacatacctc gctctgctaa tcctgttacc 1860
agtggctgct gccagtggcg ataagtcgtg tcttaccggg ttggactcaa gacgatagtt 1920
accggataag gcgcagcggt cgggctgaac ggggggttcg tgcacacagc ccagcttgga 1980
gcgaacgacc tacaccgaac tgagatacct acagcgtgag ctatgagaaa gcgccacgct 2040
tcccgaaggg agaaaggcgg acaggtatcc ggtaagcggc agggtcggaa caggagagcg 2100
cacgagggag cttccagggg gaaacgcctg gtatctttat agtcctgtcg ggtttcgcca 2160
cctctgactt gagcgtcgat ttttgtgatg ctcgtcaggg gggcggagcc tatggaaaaa 2220
cgccagcaac gcggcctttt tacggttcct ggccttttgc tggccttttg ctcacatgtt 2280
ctttcctgcg ttatcccctg attctgtgga taaccgtatt accgcctttg agtgagctga 2340
taccgctcgc cgcagccgaa cgaccgagcg cagcgagtca gtgagcgagg aagcggaaga 2400
gcgcctgatg cggtattttc tccttacgca tctgtgcggt atttcacacc gcatatatgg 2460
tgcactctca gtacaatctg ctctgatgcc gcatagttaa gccagtatac actccgctat 2520
cgctacgtga ctgggtcatg gctgcgcccc gacacccgcc aacacccgct gacgcgccct 2580
gacgggcttg tctgctcccg gcatccgctt acagacaagc tgtgaccgtc tccgggagct 2640
gcatgtgtca gaggttttca ccgtcatcac cgaaacgcgc gaggcagctg cggtaaagct 2700
catcagcgtg gtcgtgaagc gattcacaga tgtctgcctg ttcatccgcg tccagctcgt 2760
tgagtttctc cagaagcgtt aatgtctggc ttctgataaa gcgggccatg ttaagggcgg 2820
ttttttcctg tttggtcact gatgcctccg tgtaaggggg atttctgttc atgggggtaa 2880
tgataccgat gaaacgagag aggatgctca cgatacgggt tactgatgat gaacatgccc 2940
ggttactgga acgttgtgag ggtaaacaac tggcggtatg gatgcggcgg gaccagagaa 3000
aaatcactca gggtcaatgc cagcgcttcg ttaatacaga tgtaggtgtt ccacagggta 3060
gccagcagca tcctgcgatg cagatccgga acataatggt gcagggcgct gacttccgcg 3120
tttccagact ttacgaaaca cggaaaccga agaccattca tgttgttgct caggtcgcag 3180
acgttttgca gcagcagtcg cttcacgttc gctcgcgtat cggtgattca ttctgctaac 3240
cagtaaggca accccgccag cctagccggg tcctcaacga caggagcacg atcatgcgca 3300
```

FIG. 7

```
cccgtggcca ggacccaacg ctgcccgaga tctcgatccc gcgaaattaa tacgactcac 3360
tatagggaga ccacaacggt ttccctctag aaataatttt gtttaacttt aagaaggaga 3420
tatacat atg agt gca aaa ggc ata gac tac gat aag ctc att gtt cgg   3469
ttt gga agt agt aaa att gac aaa gag cta ata aac cga ata gag aga   3517
gcc acc ggc caa aga cca cac cac ttc ctg cgc aga ggc atc ttc ttc   3565
tca cac aga gat atg aat cag gtt ctt gat gcc tat gaa aat aag aag   3613
cca ttt tat ctg tac acg ggc cgg ggc ccc tct tct gaa gca atg cat   3661
gta ggt cac ctc att cca ttt att ttc aca aag tgg ctc cag gat gta   3709
ttt aac gtg ccc ttg gtc atc cag atg acg gat gac gag aag tat ctg   3757
tgg aag gac ctg acc ctg gac cag gcc tat ggc gat gct gtt gag aat   3805
gcc aag gac atc atc gcc tgt ggc ttt gac atc aac aag act ttc ata   3853
ttc tct gac ctg gac tac atg ggg atg agc tca ggt ttc tac aaa aat   3901
gtg gtg aag att caa aag cat gtt acc ttc aac caa gtg aaa ggc att   3949
ttc ggc ttc act gac agc gac tgc att ggg aag atc agt ttt cct gcc   3997
atc cag gct gct ccc tcc ttc agc aac tca ttc cca cag atc ttc cga   4045
gac agg acg gat atc cag tgc ctt atc cca tgt gcc att gac cag gat   4093
cct tac ttt aga atg aca agg gac gtc gcc ccc agg atc ggc tat cct   4141
aaa cca gcc ctg ttg cac tcc acc ttc ttc cca gcc ctg cag ggc gcc   4189
cag acc aaa atg agt gcc agc gac cca aac tcc tcc atc ttc ctc acc   4237
gac acg gcc aag cag atc aaa acc aag gtc aat aag cat gcg ttt tct   4285
gga ggg aga gac acc atc gag gag cac agg cag ttt ggg ggc aac tgt   4333
gat gtg gac gtg tct ttc atg tac ctg acc ttc ttc ctc gag gac gac   4381
gac aag ctc gag cag atc agg aag gat tac acc agc gga gcc atg ctc   4429
acc ggt gag ctc aag aag gca ctc ata gag gtt ctg cag ccc ttg atc   4477
gca gag cac cag gcc cgg cgc aag gag gtc acg gat gag ata gtg aaa   4525
gag ttc atg act ccc cgg aag ctg tcc ttc gac ttt cag aag ctt gcg   4573
gcc gca ctc gag cac cac cac cac cac cac tgagatccgg ctgctaacaa     4623
agcccgaaag gaagctgagt tggctgctgc caccgctgag caataactag cataacccct 4683
tggggcctct aaacgggtct tgaggggttt tttgctgaaa ggaggaacta tatccggat  4742
```

FIG. 7 Cont.

His-tagged T2 fragment of human TrpRS

```
Met Ser Ala Lys Gly Ile Asp Tyr Asp Lys Leu Ile Val Arg Phe Gly
 1               5                  10                  15
Ser Ser Lys Ile Asp Lys Glu Leu Ile Asn Arg Ile Glu Arg Ala Thr
            20                  25                  30
Gly Gln Arg Pro His His Phe Leu Arg Arg Gly Ile Phe Phe Ser His
        35                  40                  45
Arg Asp Met Asn Gln Val Leu Asp Ala Tyr Glu Asn Lys Lys Pro Phe
    50                  55                  60
Tyr Leu Tyr Thr Gly Arg Gly Pro Ser Ser Glu Ala Met His Val Gly
65                  70                  75                  80
His Leu Ile Pro Phe Ile Phe Thr Lys Trp Leu Gln Asp Val Phe Asn
                85                  90                  95
Val Pro Leu Val Ile Gln Met Thr Asp Asp Glu Lys Tyr Leu Trp Lys
            100                 105                 110
Asp Leu Thr Leu Asp Gln Ala Tyr Gly Asp Ala Val Glu Asn Ala Lys
        115                 120                 125
Asp Ile Ile Ala Cys Gly Phe Asp Ile Asn Lys Thr Phe Ile Phe Ser
    130                 135                 140
Asp Leu Asp Tyr Met Gly Met Ser Ser Gly Phe Tyr Lys Asn Val Val
145                 150                 155                 160
Lys Ile Gln Lys His Val Thr Phe Asn Gln Val Lys Gly Ile Phe Gly
                165                 170                 175
Phe Thr Asp Ser Asp Cys Ile Gly Lys Ile Ser Phe Pro Ala Ile Gln
            180                 185                 190
Ala Ala Pro Ser Phe Ser Asn Ser Phe Pro Gln Ile Phe Arg Asp Arg
        195                 200                 205
Thr Asp Ile Gln Cys Leu Ile Pro Cys Ala Ile Asp Gln Asp Pro Tyr
    210                 215                 220
Phe Arg Met Thr Arg Asp Val Ala Pro Arg Ile Gly Tyr Pro Lys Pro
225                 230                 235                 240
Ala Leu Leu His Ser Thr Phe Phe Pro Ala Leu Gln Gly Ala Gln Thr
                245                 250                 255
Lys Met Ser Ala Ser Asp Pro Asn Ser Ser Ile Phe Leu Thr Asp Thr
            260                 265                 270
Ala Lys Gln Ile Lys Thr Lys Val Asn Lys His Ala Phe Ser Gly Gly
        275                 280                 285
Arg Asp Thr Ile Glu Glu His Arg Gln Phe Gly Gly Asn Cys Asp Val
    290                 295                 300
Asp Val Ser Phe Met Tyr Leu Thr Phe Phe Leu Glu Asp Asp Asp Lys
305                 310                 315                 320
Leu Glu Gln Ile Arg Lys Asp Tyr Thr Ser Gly Ala Met Leu Thr Gly
                325                 330                 335
Glu Leu Lys Lys Ala Leu Ile Glu Val Leu Gln Pro Leu Ile Ala Glu
            340                 345                 350
His Gln Ala Arg Arg Lys Glu Val Thr Asp Glu Ile Val Lys Glu Phe
        355                 360                 365
Met Thr Pro Arg Lys Leu Ser Phe Asp Phe Gln Lys Leu Ala Ala Ala
    370                 375                 380
Leu Glu His His His His His His
385                 390
```

FIG. 8

HEMATOPOIETIC STEM CELLS AND METHODS OF TREATMENT OF NEOVASCULAR EYE DISEASES THEREWITH

CROSS-REFERENCE TO RELATED APPLICATIONS

This application claims the benefit of Provisional Application for Patent Ser. No. 60/398,522, filed on Jul. 25, 2002, and Provisional Application for Patent Ser. No. 60/467,051, filed on May 2, 2003, both of which are incorporated herein by reference.

STATEMENT OF GOVERNMENT INTEREST

This invention was made with U.S. Government support under grant number CA92577 from the National Cancer Institute and under grants number EY11254, EY12598 and EY12599 from the National Institutes of Health. The U.S. Government has certain rights in this invention.

FIELD OF THE INVENTION

This invention relates to isolated, mammalian, lineage negative hematopoietic stem cells ($Lin^-$ HSC) derived from bone marrow. The invention also relates to treatment of vascular diseases of the eye by administering $Lin^-$ HSC and transfected $Lin^-$ HSC to the retina.

BACKGROUND OF THE INVENTION

Age Related Macular Degeneration (ARMD) and Diabetic Retinopathy (DR) are the leading causes of visual loss in industrialized nations and do so as a result of abnormal retinal neovascularization. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa (RP), are also associated with vascular abnormalities, such as arteriolar narrowing and vascular atrophy. While significant progress has been made in identifying factors that promote and inhibit angiogenesis, no treatment is currently available to specifically treat ocular vascular disease.

For many years it has been known that a population of stem cells exists in the normal adult circulation and bone marrow. Different sub-populations of these cells can differentiate along hematopoietic lineage positive ($Lin^+$) or non-hematopoietic, lineage negative ($Lin^-$) lineages. Furthermore, the lineage negative hematopoietic stem cell (HSC) population has recently been shown to contain endothelial progenitor cells (EPC) capable of forming blood vessels in vitro and in vivo. Asahara et al. *Science* 275, 964–7 (1997). These cells can participate in normal and pathological postnatal angiogenesis (See Lyden et al. *Nat. Med.* 7, 1194–201 (2001); Kalka et al. *Proc. Natl. Acad. Sci. U.S.A.* 97, 3422–7 (2000); and Kocher et al. *Nat. Med.* 7, 430–6 (2001)) as well as differentiate into a variety of non-endothelial cell types including hepatocytes (See Lagasse et al. *Nat. Med.* 6, 1229–34 (2000)), microglia (See Priller et al. *Nat. Med.* 7, 1356–61 (2002)), cardiomyocytes (See Orlic et al. *Proc. Natl. Acad. Sci. U.S.A.* 98, 10344–9 (2001)) and epithelium (See Lyden et al. *Nat. Med.* 7, 1194–201 (2001)). Although these cells have been used in several experimental models of angiogenesis, the mechanism of EPC targeting to neovasculature is not known and no strategy has been identified that will effectively increase the number of cells that contribute to a particular vasculature.

SUMMARY OF THE INVENTION

The present invention provides isolated, mammalian, lineage negative hematopoietic stem cell populations ($Lin^-$ HSC) derived from bone marrow, which contain endothelial progenitor cells (EPC; also known as endothelial precursor cells) that selectively target activated retinal astrocytes. At least about 50% of the cells of the isolated $Lin^-$ HSC populations of the present invention have cell markers for CD31 and c-kit.

The EPC's in the lineage negative HSC populations of the present invention extensively incorporate into developing retinal vessels and remain stably incorporated into neovasculature of the eye. The isolated, lineage negative HSC populations of the present invention can be used to rescue and stabilize degenerating retinal vasculature in mammals. In one embodiment of the isolated $Lin^-$ HSC populations of the present invention, the cells are transfected with a therapeutically useful gene. The transfected cells can selectively target neovasculature and inhibit new vessel formation without affecting already established vessels through a form of cell-based gene therapy. Cells from isolated, lineage negative HSC population of the present invention that have been transfected with a gene encoding angiogenesis inhibiting peptides are useful for modulating abnormal blood vessel growth in diseases such as ARMD, DR and certain retinal degenerations associated with abnormal vasculature.

A particular advantage of ocular treatments with the isolated $Lin^-$ HSC population of the present invention is a vasculotrophic and neurotrophic rescue effect observed in eyes intravitreally treated with the $Lin^-$ HSC. Retinal neurons and photoreceptors are preserved and visual function is maintained in eyes treated with the isolated $Lin^-$ HSC of the invention.

The present invention also provides a method of isolating lineage negative hematopoietic stem cell populations containing endothelial progenitor cells from bone marrow, preferably adult bone marrow.

BRIEF DESCRIPTION OF THE DRAWINGS

FIG. 1*c* depicts flow cytometric characterization of bone marrow-derived $Lin^+$ HSC and $Lin^-$ HSC separated cells. Top row: Dot plot distribution of non-antibody labeled cells, in which R1 defines the quantifiable-gated area of positive PE-staining; R2 indicates GFP-positive; Middle row: $Lin^-$ HSC (C57B/6) and Bottom row: $Lin^+$ HSC (C57B/6) cells, each cell line labeled with the PE-conjugated antibodies for Sca-1, c-kit, Flk-1/KDR, CD31. Tie-2 data was obtained from Tie-2-GFP mice. Percentages indicate percent of positive-labeled cells out of total $Lin^-$ HSC or $Lin^+$ HSC population.

FIG. 7 shows the DNA sequence encoding $His_6$-tagged T2-TrpRS, SEQ ID NO: 1.

FIG. 8 shows the amino acid sequence of $His_6$-tagged T2-TrpRS, SEQ ID NO: 2.

DETAILED DESCRIPTION OF PREFERRED EMBODIMENTS

Figure 1:
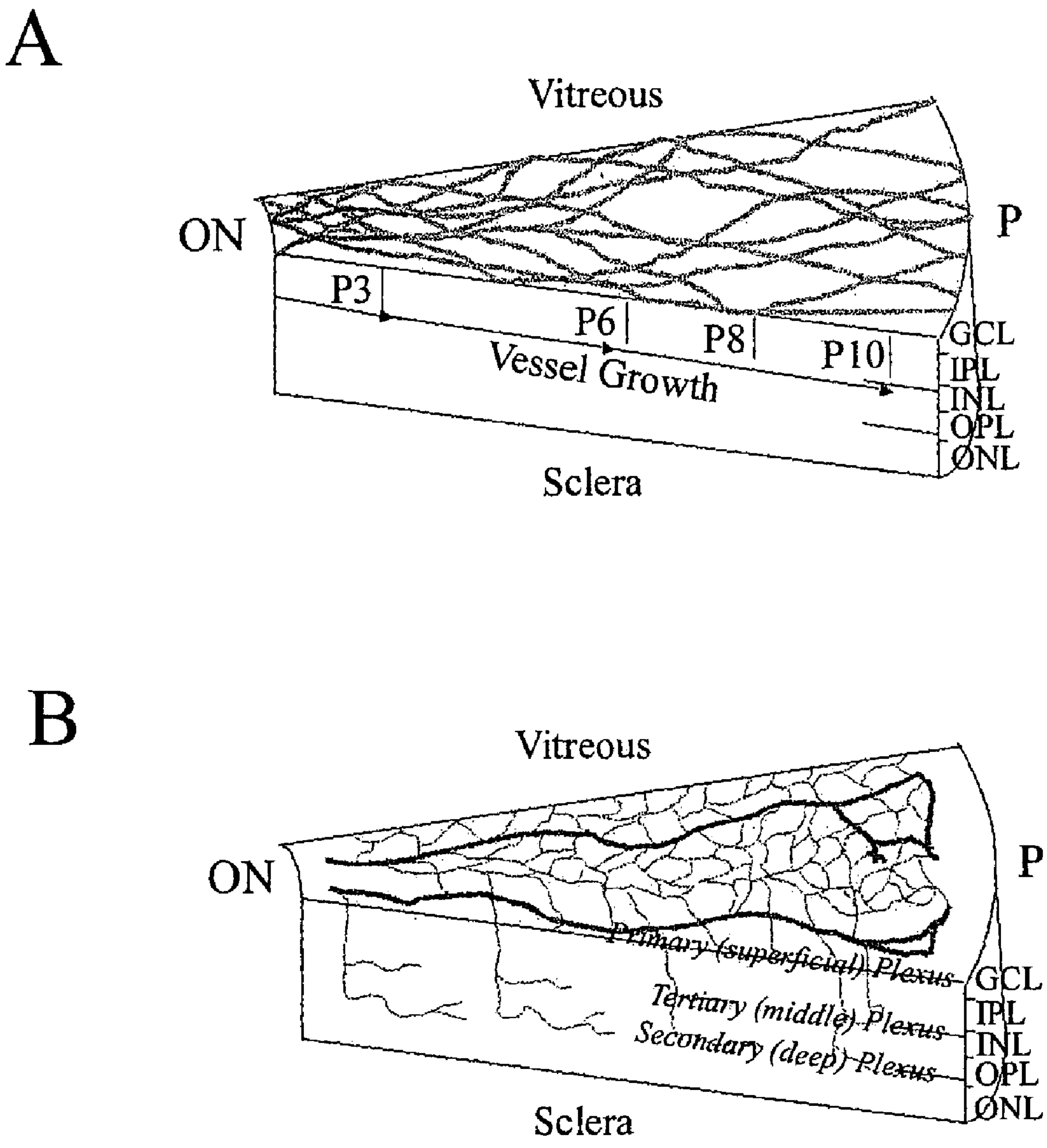
FIG. 1 (*a* and *b*) depicts schematic diagrams of developing mouse retina. (a) Development of primary plexus. (b) The second phase of retinal vessel formation. GCL, ganglion cell layer; IPL, inner plexus layer; INL, inner nuclear layer; OPL, outer plexus layer; ONL, outer nuclear layer; RPE, retinal pigment epithelium; ON, optic nerve; P, periphery.
Figure 1:
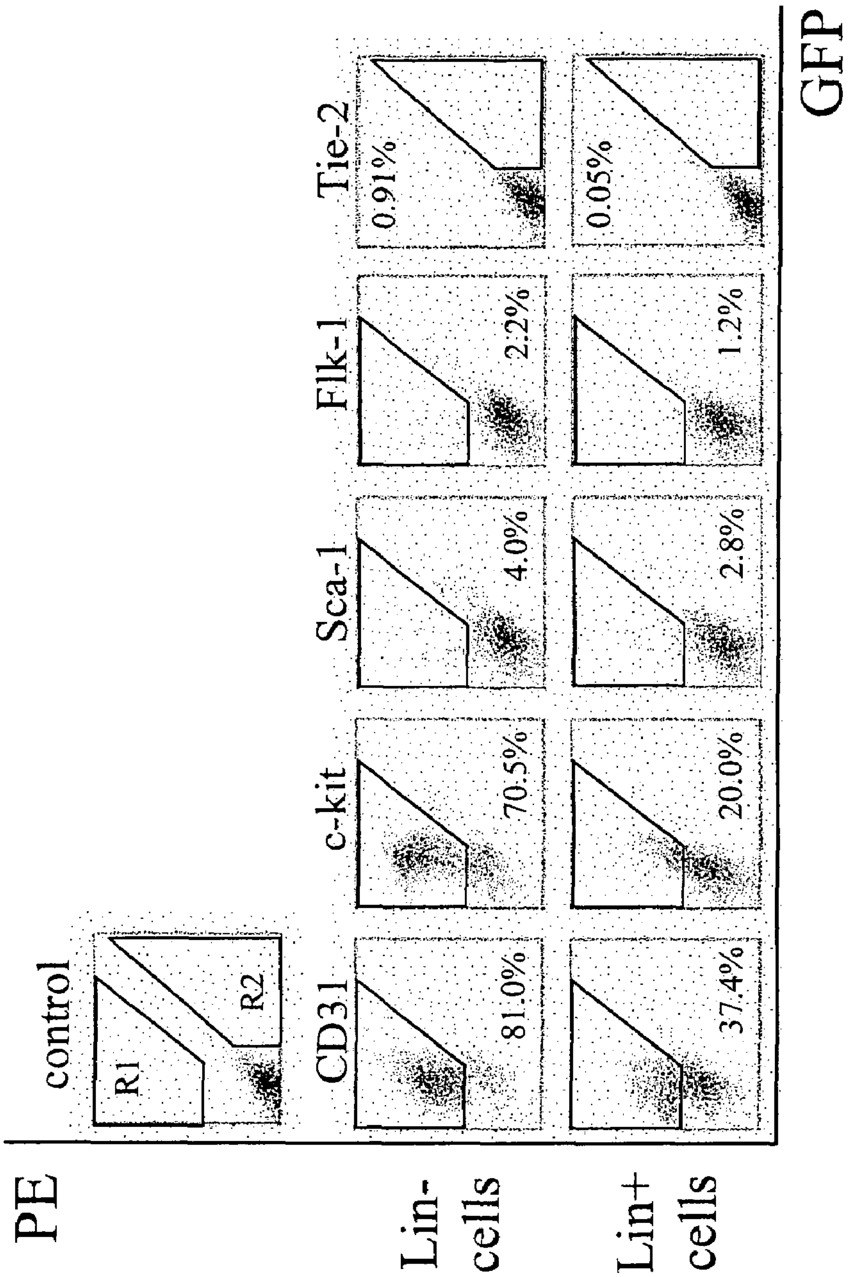

The present invention provides an isolated, mammalian, bone marrow-derived lineage negative hematopoietic stem cell population containing endothelial progenitor cells. The isolated $Lin^-$ HSC populations of the present invention preferably comprise HSC in which at least about 50% of the cells contain CD31 and c-kit cell marker antigens. In a preferred embodiment, at least about 75% of the HSC cells include the CD31 marker, more preferably about 81% of the cells. In another preferred embodiment, at least about 65% of the cells include the c-kit cells marker, more preferably about 70% of the cells.

In a particularly preferred embodiment of the isolated $Lin^-$ HSC populations of the present invention, about 50% to about 85% of the cells include the CD31 marker, about 70% to about 75% of the cells include the c-kit marker, about 4% to about 8% of the cells include the Sca-1 marker, and about 2% to about 4% of the cells include the Flk-1/KDR marker.

The isolated $Lin^-$ HSC populations of the present invention can also comprise up to about 1% of cells having the Tie-2 antigen marker.

In preferred embodiments, the isolated $Lin^-$ HSC populations of the present invention are derived from mouse or human bone marrow, preferably from human bone marrow.

The isolated $Lin^-$ HSC populations of the present invention selectively target and incorporate into the retinal neovasculature when intravitreally injected into the eye of the mammalian species from which the cells were isolated.

The isolated $Lin^-$ HSC populations of the present invention contain EPC cells that differentiate to endothelial cells and generate vascular structures within the retina. In particular, the $Lin^-$ HSC compositions of the present invention are useful for the treatment of retinal neovascular and retinal vascular degenerative diseases, and for repair of retinal vascular injury.

The present invention also provides a method of treating ocular diseases in a patient comprising isolating from the bone marrow of the patient a lineage negative hematopoietic stem cell population that includes endothelial progenitor cells, and intravitreally injecting the isolated stem cells into an eye of the patient in a number sufficient to arrest the disease. The present method can be utilized to treat ocular diseases such as retinal degenerative diseases, retinal vascular degenerative diseases, ischemic retinopathies, vascular hemorrhages, vascular leakage, and choroidopathies. Examples of such diseases include age related macular degeneration (ARMD), diabetic retinopathy (DR), presumed ocular histoplasmosis (POHS), retinopathy of prematurity (ROP), sickle cell anemia, and retinitis pigmentosa, as well as retinal injuries.

The number of stem cells injected into the eye is sufficient for arresting the disease state of the patient's eye. For example, the number of cells can be effective for repairing retinal damage of the patient's eye, stabilizing retinal neovasculature, maturing retinal neovasculature, and preventing or repairing vascular leakage and vascular hemorrhage.

Cells present in the isolated $Lin^-$ HSC populations of the present invention can be transfected with therapeutically useful genes, such as genes encoding antiangiogenic proteins for use in ocular, cell-based gene therapy.

The transfected cells can include any gene which is therapeutically useful for treatment of retinal disorders. Preferably, the transfected cells in the $Lin^-$ HSC populations of the present invention include a gene encoding an antiangiogenic peptide, protein, or protein fragment such as TrpRS or antiangiogenic fragments thereof, such as the T1 and T2 fragments thereof, which are described in detail in co-owned, co-pending U.S. patent application Ser. No. 10/080,839, the disclosure of which is incorporated herein by reference.

The present invention also provides a method of isolating a lineage negative hematopoietic stem cell population containing endothelial progenitor cells from bone marrow. The method entails the steps of (a) extracting bone marrow from a mammal; (b) separating a plurality of monocytes from the bone marrow; (c) labeling the monocytes with biotin conjugated lineage panel antibodies to CD45, CD3, Ly-6G, CD11 and TER-119; and (d) removal of monocytes that are positive for CD45, CD3, Ly-6G, CD11 and TER-119 from the plurality of monocytes to provide a population of lineage negative hematopoietic stem cells containing endothelial progenitor cells.

The present invention also provides methods for treating ocular angiogenic diseases by administering transfected $Lin^-$ HSC compositions of the present invention by intravitreal injection of the cells into the eye. Such transfected $Lin^-$ HSC compositions comprise $Lin^-$ HSC transfected with a therapeutically useful gene, such as a gene encoding anti-angiogram gene product.

Preferably, at least about $1\times10^5$ $Lin^-$ HSC cells or transfected $Lin^-$ HSC cells are administered by intravitreal injection to an eye suffering from a retinal degenerative disease. The number of cells to be injected may depend upon the severity of the retinal degeneration, the age of the patient and other factors that will be readily apparent to one of ordinary skill in the art of treating retinal diseases. The $Lin^-$ HSC may be administered in a single dose or by multiple dose administration over a period of time, as determined by the physician in charge of the treatment.

The $Lin^-$ HSC populations of the present invention are useful for the treatment of retinal injuries and retinal defects involving an interruption in or degradation of the retinal vasculature.

The transfected $Lin^-$ HSC populations of the present invention are useful for delivery of therapeutic genes to the retina, particularly to the retinal vasculature.

In a preferred embodiment of the gene delivery method of the present invention, cells in the $Lin^-$ HSC populations of the present invention are transfected with a gene encoding an antiangiogenic peptide such as antiangiogenic fragment of tryptophan RNA synthetase (TrpRS). Particularly preferred fragments of TrpRS include the T1 and T2 fragments of TrpRS. The transfected cells in the $Lin^-$ HSC compositions encoding an antiangiogenic peptide of the present invention are useful for treatment of retinal disease involving abnormal vascular development, such as Diabetic Retinopathy and like diseases.

Methods

EXAMPLE 1

Cell Isolation and Enrichment; Preparation of a $Lin^-$ HSC Populations A and B General Procedure. All in vivo evaluations were performed in accordance with the NIH Guide for the Care and Use of Laboratory Animals, and all evaluation procedures were approved by The Scripps Research Institute (TSRI, La Jolla, Calif.) Animal Care and Use Committee. Bone marrow cells were extracted from B6.129S7-Gtrosa26; Tie-2GFP, ACTbEGFP, FVB/NJ (rd/rd mice) or Balb/cBYJ adult mice (The Jackson Laboratory, Me.).

Monocytes were then separated by density gradient separation using HISTOPAQUE® polysucrose gradient (Sigma, St. Louis, Mo.) and labeled with biotin conjugated lineage panel antibodies (CD45, CD3, Ly-6G, CD11, TER-119, Pharmingen, San Diego, Calif.) for $Lin^-$ selection. Lineage positive ($Lin^+$) cells were separated and removed from $Lin^-$ HSC using a magnetic separation device (AUTOMACS™ sorter, Miltenyi Biotech, Auburn, Calif.). The resulting $Lin^-$ HSC population, containing endothelial progenitor cells was further characterized using a FACS™ Calibur flow cytometer (Becton Dickinson, Franklin Lakes, N.J.) using following antibodies: PE-conjugated-Sca-1, c-kit, KDR, and CD31 (Pharmingen, San Diego, Calif.). Tie-2-GFP bone marrow cells were used for characterization of Tie-2.

To harvest adult mouse endothelial cells, mesenteric tissue was surgically removed from ACTbEGFP mouse and placed in collagenase (Worthington, Lakewood, N.J.) to digest the tissue, followed by filtration using a 45 μm filter. Flow-through was collected and incubated with Endothelial Growth Media (Clonetics, San Diego, Calif.). Endothelial characteristics were confirmed by observing morphological cobblestone appearance, staining with CD31 mAb (Pharmingen) and examining cultures for the formation of tube-like structures in MATRIGEL™ matrix (Beckton Dickinson, Franklin Lakes, N.J.).

$Lin^-$ HSC Population. A. Bone marrow cells were extracted from ACTbEGFP mice by the General Procedure described above. The $Lin^-$ HSC cells were characterized by FACS flow cytometry for CD31, c-kit, Sca-1, Flk-1, and Tie-2 cell surface antigen markers. The results are shown in FIG. 1*c*. About 81% of the $Lin^-$ HSC exhibited the CD31 marker, about 70.5% of the $Lin^-$ HSC exhibited the c-kit marker, about 4% of the $Lin^-$ HSC exhibited the Sca-1 marker, about 2.2% of the $Lin^-$ HSC exhibited the Flk-1 marker and about 0.91% of the $Lin^-$ HSC cell exhibited the Tie-2 marker. In contrast, the $Lin^+$ HSC that were isolated from these bone marrow cells had a significantly different cell marker profile (i.e., CD31: 37.4%; c-kit: 20%; Sca-1: 2.8%; Flk-: 0.05%).

$Lin^-$ HSC Population B. Bone marrow cells were extracted from BalbC, ACTbEGFP, and C3H mice by the General Procedure described above. The $Lin^-$ HSC cells were analyzed for the presence of cell surface markers (Sca1, KDR, cKit, CD34, CD31 and various integrins: α1, α2, α3, α4, α5, α6, $\alpha_M$, $\alpha_V$, $\alpha_X$, $\alpha_{IIb}$, $\beta_1$, $\beta_4$, $\beta_3$, $\beta_4$, $\beta_5$ and $\beta_7$). The results are shown in Table 1.

TABLE 1

Characterization of $Lin^-$ HSC Population B.

| Cell Marker | $Lin^-$ HSC |
|---|---|
| α1 | 0.10 |
| α2 | 17.57 |
| α3 | 0.22 |
| α4 | 89.39 |
| α5 | 82.47 |
| α6 | 77.70 |
| αL | 62.69 |
| αM | 35.84 |
| αX | 3.98 |
| αV | 33.64 |
| αIIb | 0.25 |
| β1 | 86.26 |
| β2 | 49.07 |
| β3 | 45.70 |
| β4 | 0.68 |
| β5 | 9.44 |
| β7 | 11.25 |
| CD31 | 51.76 |
| CD34 | 55.83 |
| Flk-1/KDR | 2.95 |
| c-kit | 74.42 |
| Sca-1 | 7.54 |

Example 2

Intravitreal Administration of Cells

An eyelid fissure was created with a fine blade to expose the P2 to P6 eyeball. Lineage negative HSC Population A of the present invention (approximately $10^5$ cells in about 0.5 μl to about 1 μl of cell culture medium) was then injected intravitreally using a 33-gauge (Hamilton, Reno, Nev.) needled-syringe.

Example 3

EPC Transfection $Lin^-$ HSC (Population A) were transfected with DNA encoding the T2 fragment of TrpRS also enclosing a $His_6$ tag (SEQ ID NO: 1, FIG. 7) using FuGENE™6 Transfection Reagent (Roche, Indianapolis, Ind.) according to manufacturer's protocol. Cells from a $Lin^-$ HSC composition (about $10^6$ cell per ml) were suspended in opti-MEM® medium (Invitrogen, Carlsbad, Calif.) containing stem cell factor (PeproTech, Rocky Hill, N.J.). DNA (about 1 μg) and FuGENE reagent (about 3 μl) mixture was then added, and the mixtures were incubated at about 37° C. for about 18 hours. After incubation, cells were washed and collected. The transfection rate of this system was approximately 17% that was confirmed by FACS analysis. T2 production was confirmed by western blotting. The amino acid sequence of $His_6$-tagged T2-TrpRS is shown as SEQ ID NO: 2, FIG. 8.

Example 4

Immunohistochemistry and Confocal Analysis

Retinas were harvested at various time points and were prepared for either whole mounting or frozen sectioning. For whole mounts, retinas were fixed with 4% paraformaldehyde, and blocked in 50% fetal bovine serum (FBS) and 20% normal goat serum for one hour at ambient room temperature. Retinas were processed for primary antibodies and detected with secondary antibodies. The primaries used were: anti-Collagen IV (Chemicon, Temecula, Calif., anti-β-gal (Promega, Madison, Wis.), anti-GFAP (Dako Cytomation, Carpenteria, Calif.), anti-α-smooth muscle actin (α-SMA, Dako Cytomation). Secondary antibodies used were conjugated either to Alexa 488 or 594 fluorescent markers (Molecular Probes, Eugene, Oreg.). Images were taken using an MRC 1024 Confocal microscope (Bio-Rad, Hercules, Calif.). Three-dimensional images were created using LASERSHARP® software (Bio-Rad) to examine the three different layers of vascular development in the whole mount retina. The difference in GFP pixel intensity between enhanced GFP (eGFP) mice and GFAP/wtGFP mice, distinguished by confocal microscopy was utilized to create the 3D images.

Example 5

In vivo Retinal Angiogenesis Quantification Assay

For T2-TrpRS analysis, the primary and deep plexus were reconstructed from the three dimensional images. Primary plexus was divided into two categories: normal development, or halted vascular progression. The categories of inhibition of deep vascular development were construed based upon the percentage of vascular inhibition including the following criteria: complete inhibition of deep plexus formation was labeled "Complete", normal vascular development (including less than 25% inhibition) was labeled "Normal" and the remainder labeled "Partial." For the rd/rd mouse rescue data, four separate areas of the deeper plexus in each whole mounted retina were captured using a 10× lens. The total length of vasculature was calculated for each image, summarized and compared between the groups. To acquire accurate information, $Lin^-$ HSC were injected into one eye and $Lin^+$ HSC into another eye of the same mouse. Non-injected control retinas were taken from the same litter.

Example 6

Adult Retinal Injury Models

Laser and scar models were created using either a diode laser (150 mW, 1 second, 50 mm) or mechanically by puncturing the retina with a 27 gauge needle. Five days after injury, cells were injected using the intravitreal method. Eyes were harvested five days later.

Example 7

Neurotrophic Rescue of Retinal Regeneration

Figure 9:
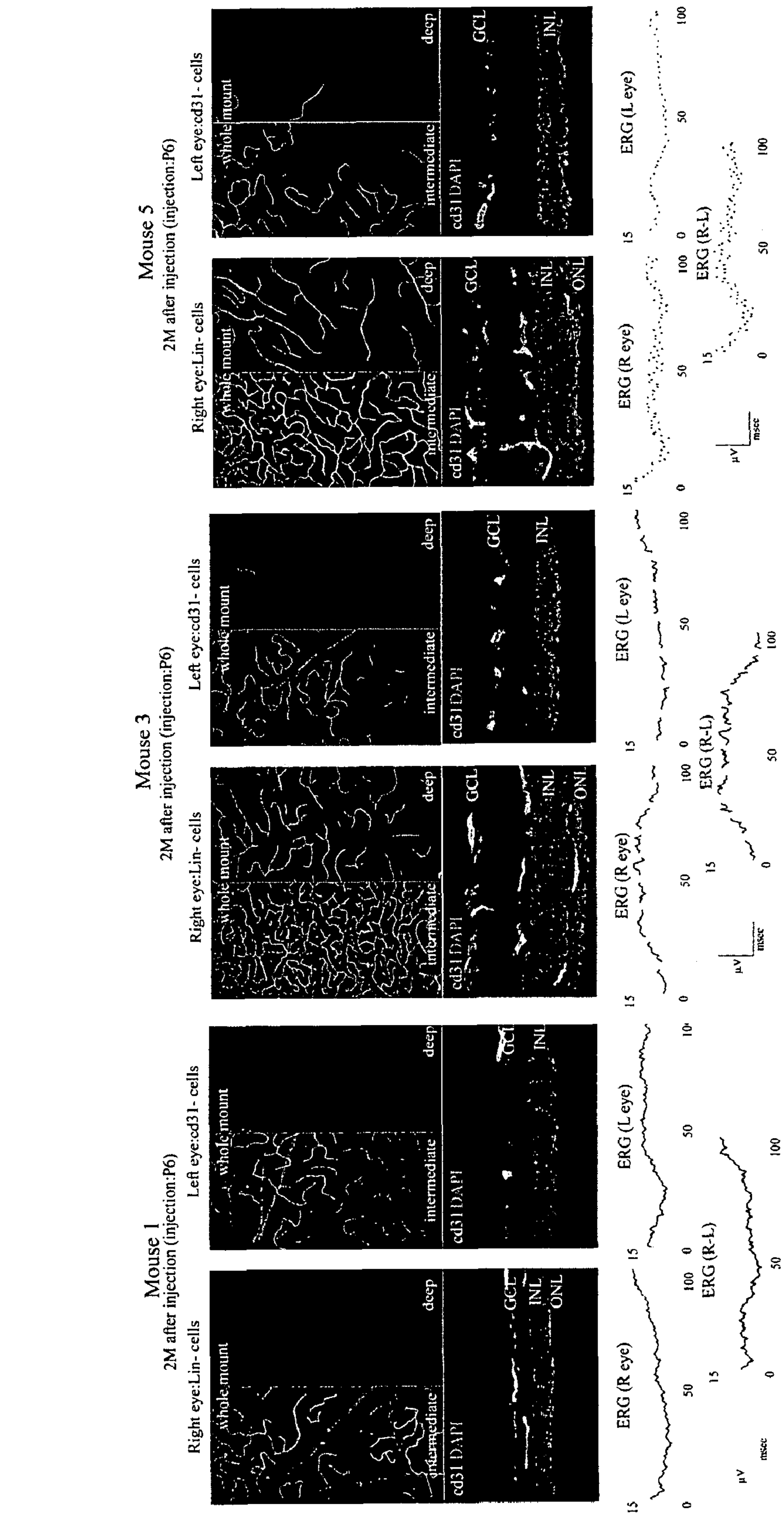
FIG. 9 illustrates photomicrographs and electroretinograms (ERG) of retinas from mice whose eyes were injected with the $Lin^-$ HSC of the present invention and with $Lin^+$ HSC (controls).

Adult bone marrow derived lineage hematopoietic stem cells ($Lin^-$ HSC) have a vasculotrophic and neurotrophic rescue effect in a mouse model of retinal degeneration. Right eyes of 10-day old mice were injected intravitreally with about 0.5 microliters containing about $10^5$ $Lin^-$ HSC of the present invention and evaluated 2 months later for the presence of retinal vasculature and neuronal layer nuclear count. The left eyes of the same mice were injected with about the same number of $Lin^+$ HSC as a control, and were similarly evaluated. As shown in FIG. 9, in the $Lin^-$ HSC treated eyes, the retinal vasculature appeared nearly normal, the inner nuclear layer was nearly normal and the outer nuclear layer (ONL) had about 3 to about 4 layers of nuclei. In contrast, the contralateral $Lin^+$ HSC treated eye had a markedly atrophic middle retinal vascular layer, a completely atrophic outer retinal vascular layer; the inner nuclear layer was markedly atrophic and the outer nuclear layer was completely gone. This was dramatically illustrated in Mouse 3 and Mouse 5. In Mouse 1, there was no rescue effect and this was true for approximately 15% of the injected mice.

Figure 10:
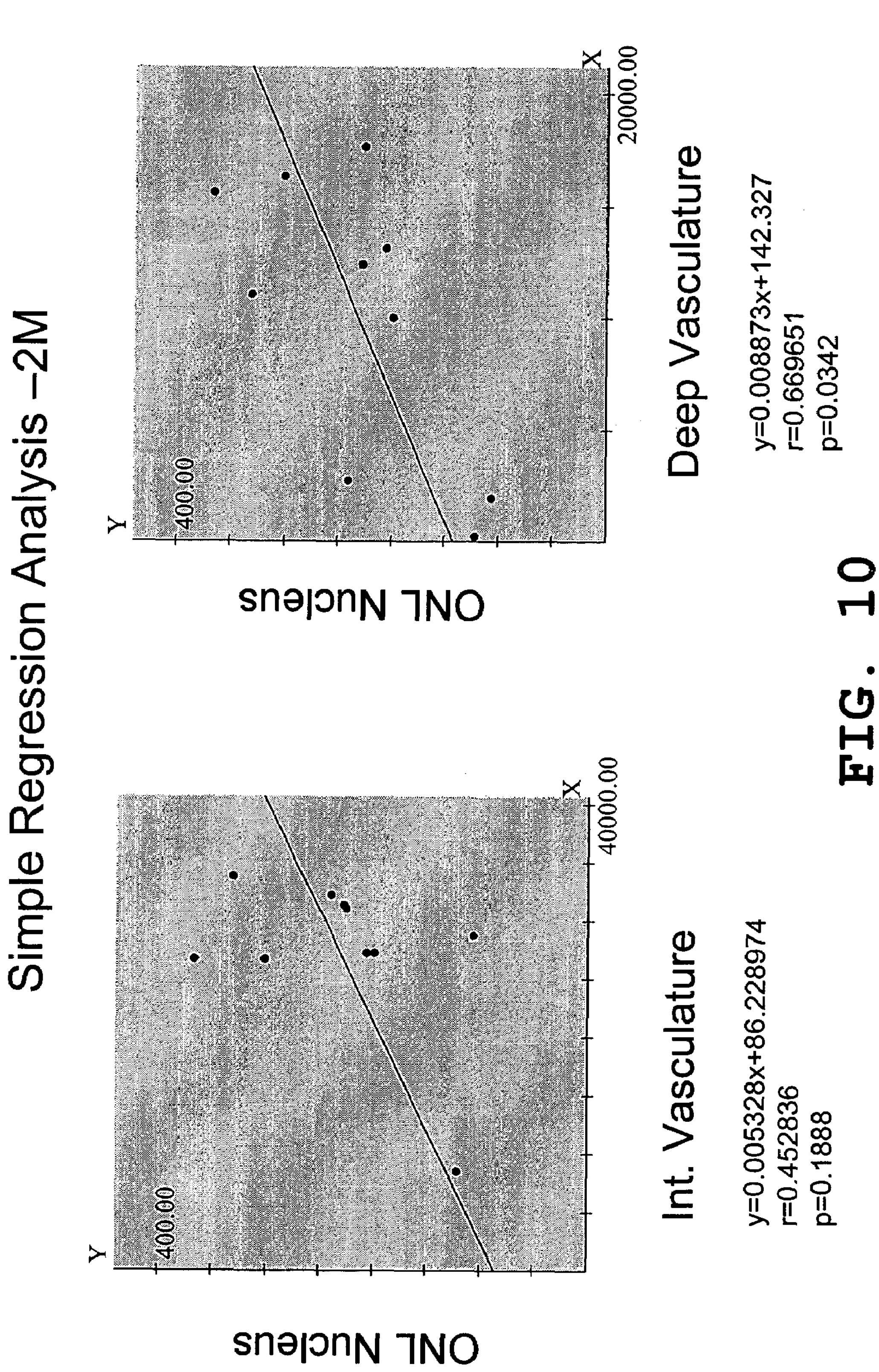
FIG. 10 depicts statistical plots showing a correlation between neuronal rescue (y-axis) and vascular rescue x-axis) for both the intermediate (Int.) and deep vascular layers of rd/rd mouse eyes treated with $Lin^-$ HSC.

When visual function was assessed with electroretinograms (ERG), the restoration of a positive ERG was observed when both the vascular and neuronal rescue was observed (Mice 3 and 5). Positive ERG was not observed when there was no vascular or neuronal rescue (Mouse 1). This correlation between vascular and neurotrophic rescue of the rd/rd mouse eyes by the $Lin^-$ HSC of the present invention is illustrated by a regression analysis plot shown in FIG. 10. A correlation between neuronal (y-axis) and vascular x-axis) recovery was observed for the intermediate vasculature type (r=0.45) and for the deep vasculature (r=0.67).

Figure 11:
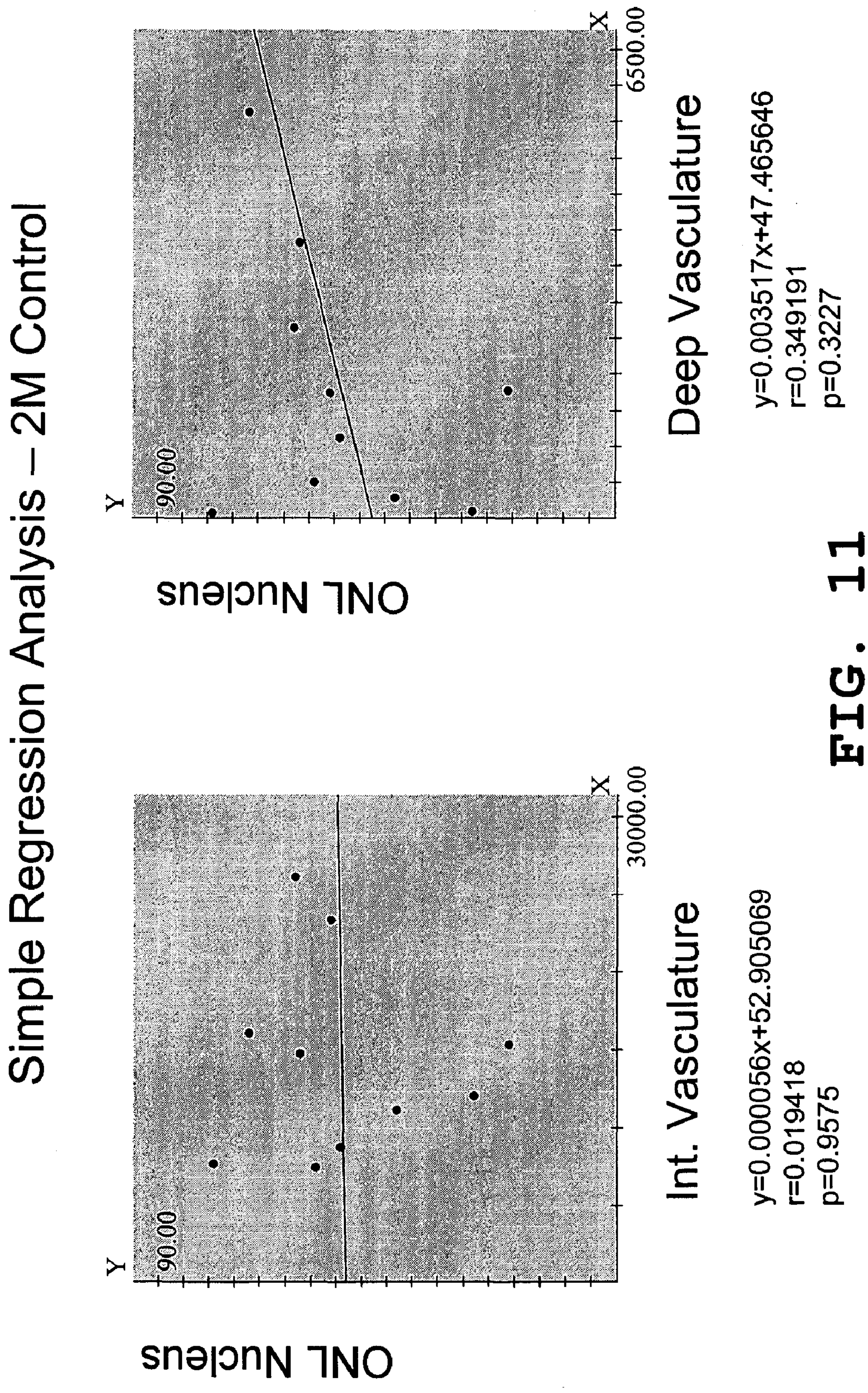
FIG. 11 depicts statistical plots showing no correlation between neuronal rescue (y-axis) and vascular rescue x-axis) for rd/rd mouse eyes that were treated with $Lin^+$ HSC.
Figure 12:
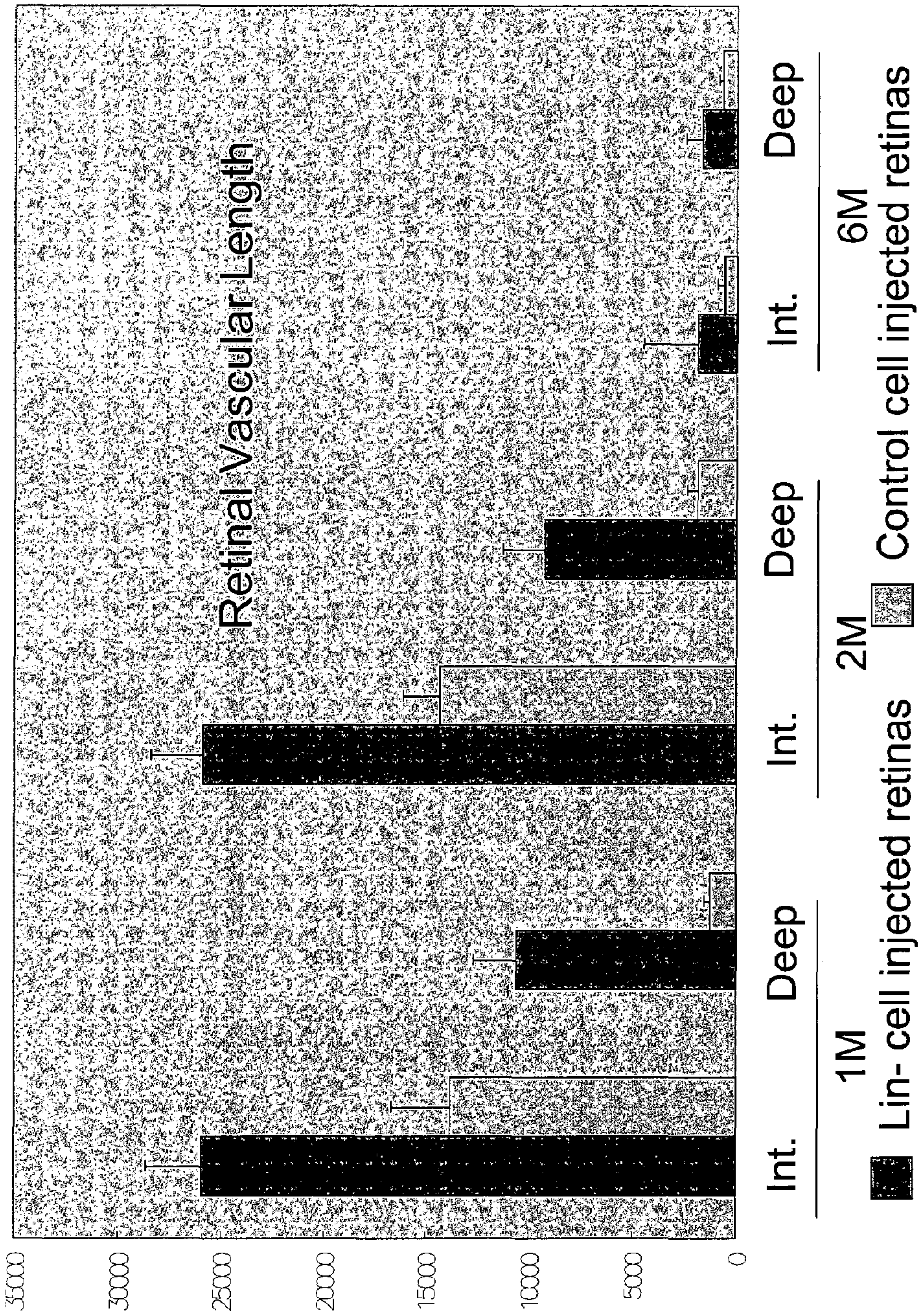
FIG. 12 is a bar graph of vascular length (y-axis) in arbitrary relative units for rd/rd mouse eyes treated with the $Lin^-$ HSC (dark bars) and untreated (light bars) rd/rd mouse eyes at time points of 1 month (1M), 2 months (2M), and 6 months (6M) post-injection.
Figure 13:
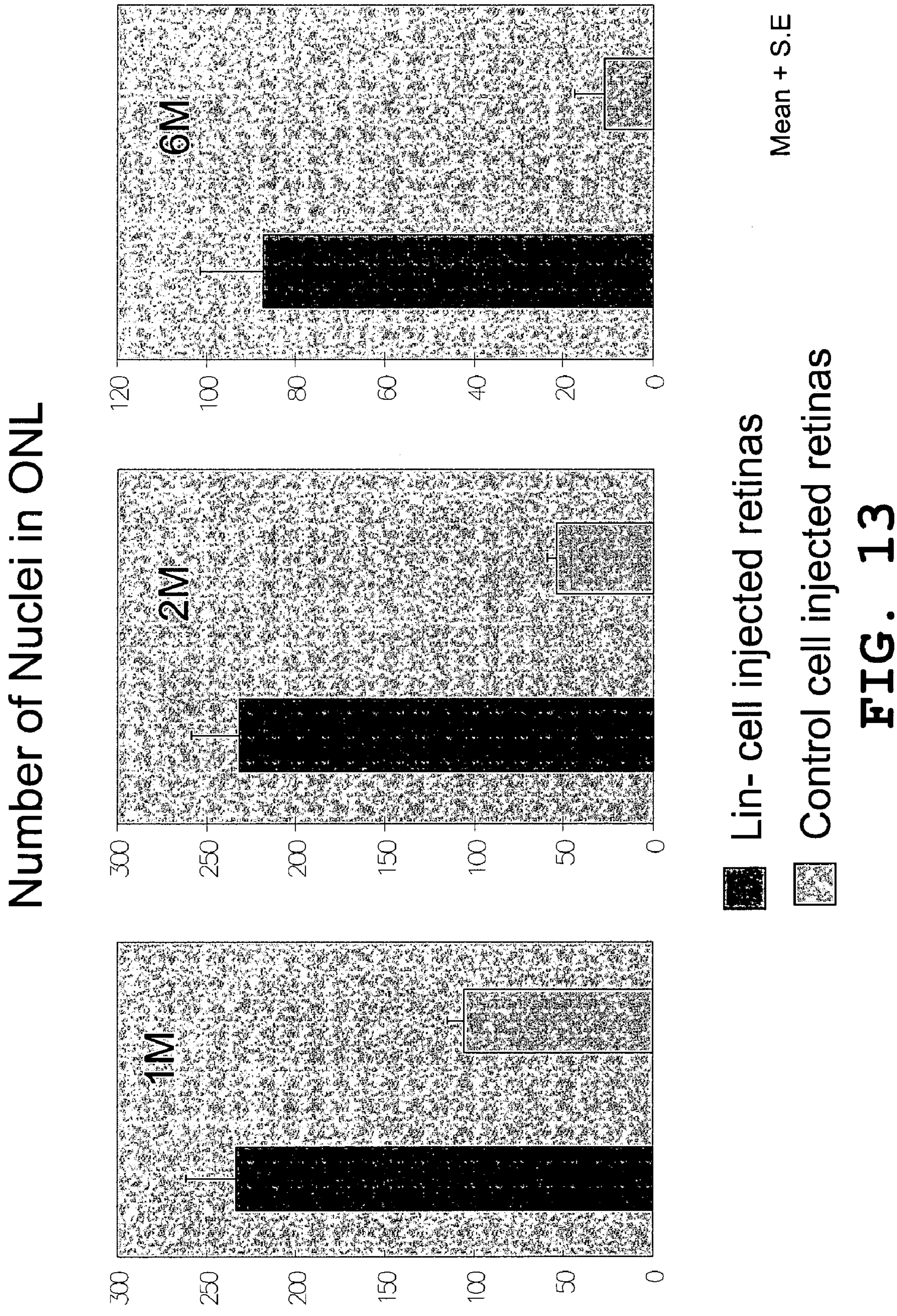
FIG. 13 includes three bar graphs of the number of nuclei in the outer neural layer (ONR) of rd/rd mice at 1 month (1M), 2 months (2M) and 6 months (6M), post-injection, and demonstrates a significant increase in the number of nuclei for eyes treated with $Lin^-$ HSC (dark bars) relative to control eyes treated with $Lin^+$ HSC (light bars).
Figure 14:
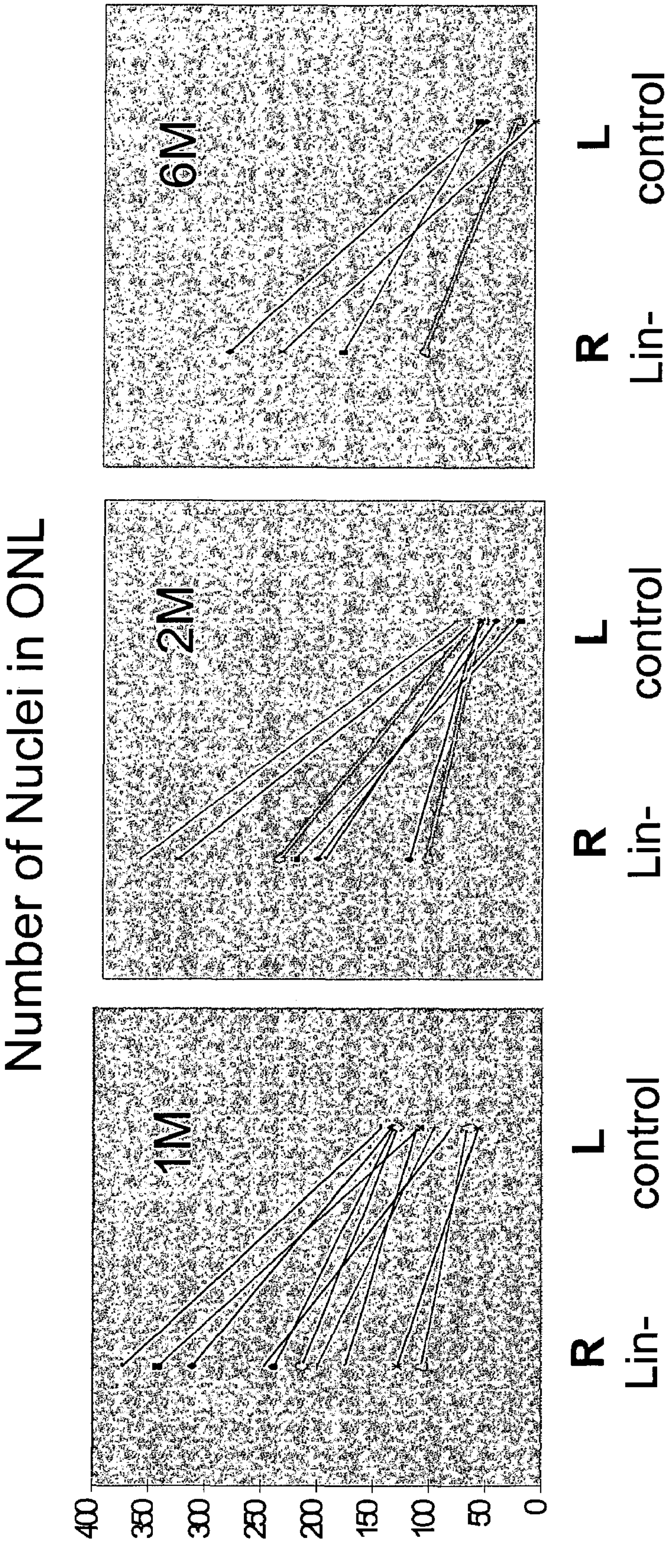
FIG. 14 depicts plots of the number of nuclei in the outer neural layer for individual rd/rd mice, comparing the right eye (R, treated with $Lin^-$ HSC) relative to the left eye (L, control eye treated with $Lin^+$ HSC) at time points (post injection) of 1 month (1M), 2 months (2M), and 6 months (6M); each line in a given plot compares the eyes of an individual mouse.

FIG. 11 shows the absence of any statistically significant correlation between vascular and neuronal rescue by $Lin^+$ HSC. The vascular rescue was quantified and the data are presented in FIG. 12. Data for mice at 1 month (1M), 2 months (2M), and 6 months (6M), post-injection shown in FIG. 12, demonstrate that vascular length was significantly increased in eyes treated with the $Lin^-$ HSC of the present invention (dark bars) relative to the vascular length in untreated eyes from the same mouse (light bars), particularly at 1 month and 2 months, post-injection. The neurotrophic rescue effect was quantified by counting nuclei in the inner and outer nuclear layers about two months after injection of $Lin^-$ HSC or $Lin^+$ HSC. The results are presented in FIGS. 13 and 14.

Results.

Murine Retinal Vascular Development; A Model for Ocular Angiogenesis

The mouse eye provides a recognized model for the study of mammalian retinal vascular development, such as human retinal vascular development. During development of the murine retinal vasculature, ischemia-driven retinal blood vessels develop in close association with astrocytes. These glial elements migrate onto the third trimester human fetus, or the neonatal rodent, retina from the optic disc along the ganglion cell layer and spread radially. As the murine retinal vasculature develops, endothelial cells utilize this already established astrocytic template to determine the retinal vascular pattern (See FIGS. 1*a* and *b*). FIG. 1 (*a* and *b*) depicts schematic diagrams of developing mouse retina. FIG. 1*a* depicts development of the primary plexus (dark lines at upper left of the diagram) superimposed over the astrocyte template (light lines) whereas, FIG. 1*b* depicts the second phase of retinal vessel formation. In the Figures, GCL stands for ganglion cell layer; IPL stands for inner plexus layer; INL stands for inner nuclear layer; OPL stands for outer plexus layer; ONL stands for outer nuclear layer; RPE stands for retinal pigment epithelium; ON stands for optic nerve; and P stands for periphery.

At birth, retinal vasculature is virtually absent. By postnatal day 14 (P14) the retina has developed complex primary (superficial) and secondary (deep) layers of retinal vessels coincident with the onset of vision. Initially, spoke-like peripapillary vessels grow radially over the pre-existing astrocytic network towards the periphery, becoming progressively interconnected by capillary plexus formation. These vessels grow as a monolayer within the nerve fiber through P10 (FIG. 1*a*). Between P7–P8 collateral branches begin to sprout from this primary plexus and penetrate into the retina to the outer plexiform layer where they form the secondary, or deep, retinal plexus. By P21, the entire network undergoes extensive remodeling and a tertiary, or intermediate, plexus forms at the inner surface of inner nuclear layer (FIG. 1*b*).

The neonatal mouse retinal angiogenesis model is useful for studying the role of HSC during ocular angiogenesis for several reasons. In this physiologically relevant model, a large astrocytic template exists prior to the appearance of endogenous blood vessels, permitting an evaluation of the role for cell-cell targeting during a neovascular process. In addition, this consistent and reproducible neonatal retinal vascular process is known to be hypoxia-driven, in this respect having similarities to many retinal diseases in which ischemia is known to play a role.

Enrichment of Endothelial Progenitor Cells (EPC) From Bone Marrow

Although cell surface marker expression has been extensively evaluated on the EPC population found in preparations of HSC, markers that uniquely identify EPC are still poorly defined. To enrich for EPC, hematopoietic lineage marker positive cells ($Lin^+$), i.e., B lymphocytes (CD45), T lymphocytes (CD3), granulocytes (Ly-6G), monocytes (CD11), and erythrocytes (TER-119), were depleted from bone marrow mononuclear cells. Sca-1 antigen was used to further enrich for EPC. A comparison of results obtained after intravitreal injection of identical numbers of either $Lin^-$ $Sca\text{-}1^+$ cells or $Lin^-$ cells, no difference was detected between the two groups. In fact, when only $Lin^-$ $Sca\text{-}1^-$ cells were injected, far greater incorporation into developing blood vessels was observed.

The $Lin^-$ HSC of the present invention are enriched for EPC based on functional assays. Furthermore, $Lin^+$ HSC populations functionally behave quite differently from the $Lin^-$ HSC populations. Epitopes commonly used to identify EPC for each fraction (based on previously reported in vitro characterization studies) were also evaluated. While none of these markers were exclusively associated with the $Lin^-$ fraction, all were increased about 70 to about 1800% in the $Lin^-$ HSC, compared to the $Lin^+$ HSC fraction (FIG. 1*c*). FIG. 1*c* illustrates flow cytometric characterization of bone marrow-derived $Lin^+$ HSC and $Lin^-$ HSC separated cells. The top row of FIG. 1*c* shows a hematopoietic stem cell dot plot distribution of non-antibody labeled cells. R1 defines the quantifiable-gated area of positive PE-staining; R2 indicates GFP-positive. Dot plots of $Lin^-$ HSC are shown in the middle row and dot plots of $Lin^+$ HSC are shown in the bottom row. The C57B/6 cells were labeled with the PE-conjugated antibodies for Sca-1, c-kit, Flk-1/KDR, CD31. Tie-2 data was obtained from Tie-2-GFP mice. The percentages in the corners of the dot plots indicate the percent of positive-labeled cells out of total $Lin^-$ or $Lin^+$ HSC population. Interestingly, accepted EPC markers like Flk-1/KDR, Tie-2, and Sca-1 were poorly expressed and, thus, not used for further fractionation.

Figure 2:
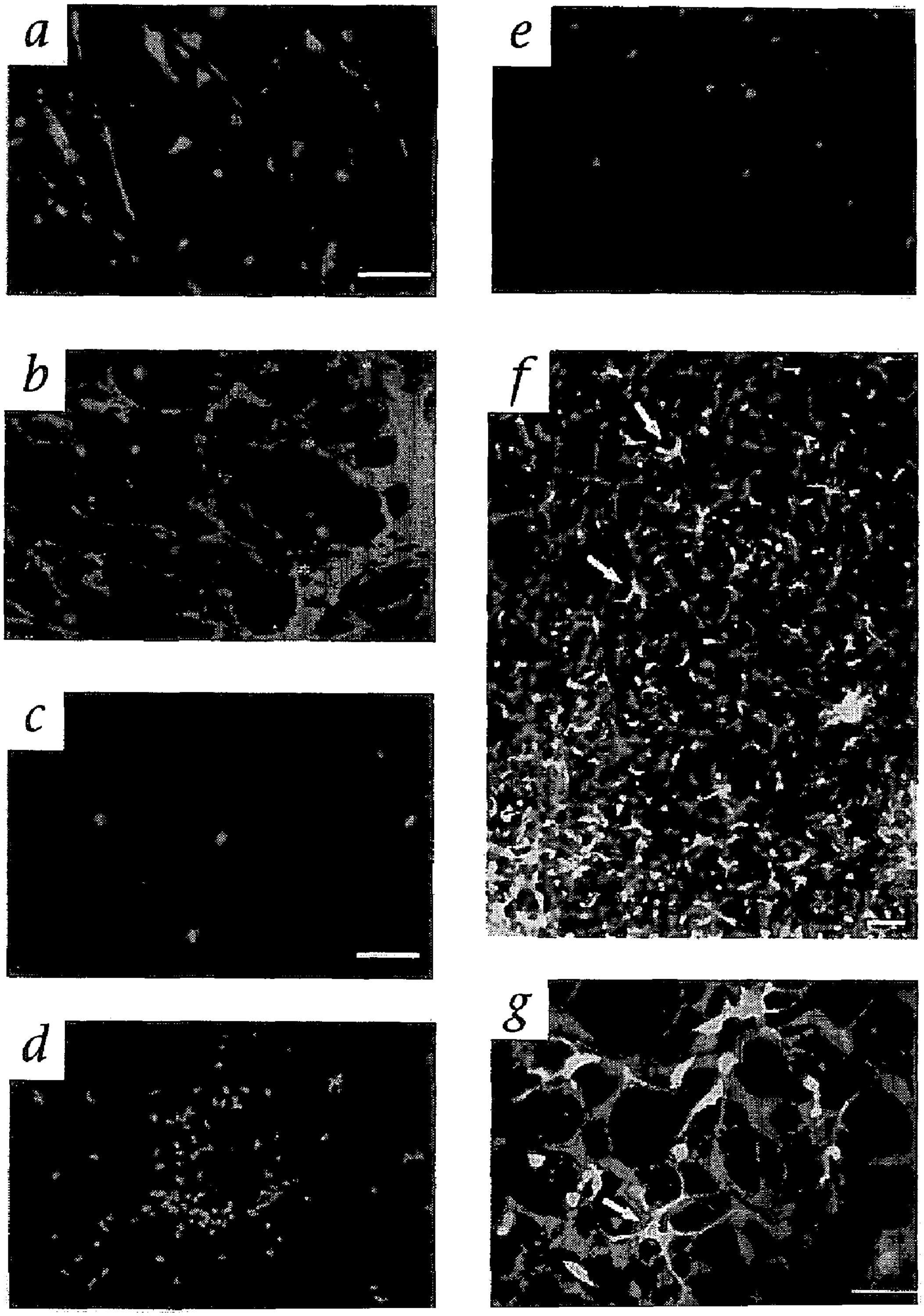
FIG. 2 depicts engraftment of $Lin^-$ HSC cells into developing mouse retina. (a) At four days post-injection (P6) intravitreally injected $eGFP^+$ $Lin^-$ HSC cells attach and differentiate on the retina (b) $Lin^-$ HSC (B6.129S7-Gtrosa26 mice, stained with β-gal antibody) establish themselves ahead of the vasculature stained with collagen IV antibody (asterisk indicates tip of vasculature). (c) Most of $Lin^+$ HSC cells ($eGFP^+$) at four days post-injection (P6) were unable to differentiate. (d) Mesenteric $eGFP^+$ murine EC four days post-injection (P6). (e) $Lin^-$ HSCs ($eGFP^+$) injected into adult mouse eyes. (f) Low magnification of $eGFP^+$ $Lin^-$ HSCs (arrows) homing to and differentiating along the pre-existing astrocytic template in the GFAP-GFP transgenic mouse. (g) Higher magnification of association between $Lin^-$ cells (eGFP) and underlying astrocyte (arrows). (h) Non-injected GFAP-GFP transgenic control. (i) Four days post-injection (P6), $eGFP^+$ $Lin^-$ HSC cells migrate to and undergo differentiation in the area of the future deep plexus. Left figure captures $Lin^-$ HSC cells activity in a whole mounted retina; right figure indicates location of the $Lin^-$ cells (arrows) in the retina (top is vitreal side, bottom is scleral side). (j) Double labeling with α-CD31-PE and α-GFP-alexa 488 antibodies. Seven days after injection, the injected $Lin^-$ HSCs (eGFP), red) were incorporated into the vasculature (CD31). Arrowheads indicate the incorporated areas. (k) $eGFP^+$ $Lin^-$ HSC cells form vessels fourteen days post-injection (P17). (l and m) Intracardiac injection of rhodamine-dextran indicates that the vessels are intact and functional in both the primary (l) and deep plexus (m).
Figure 2:
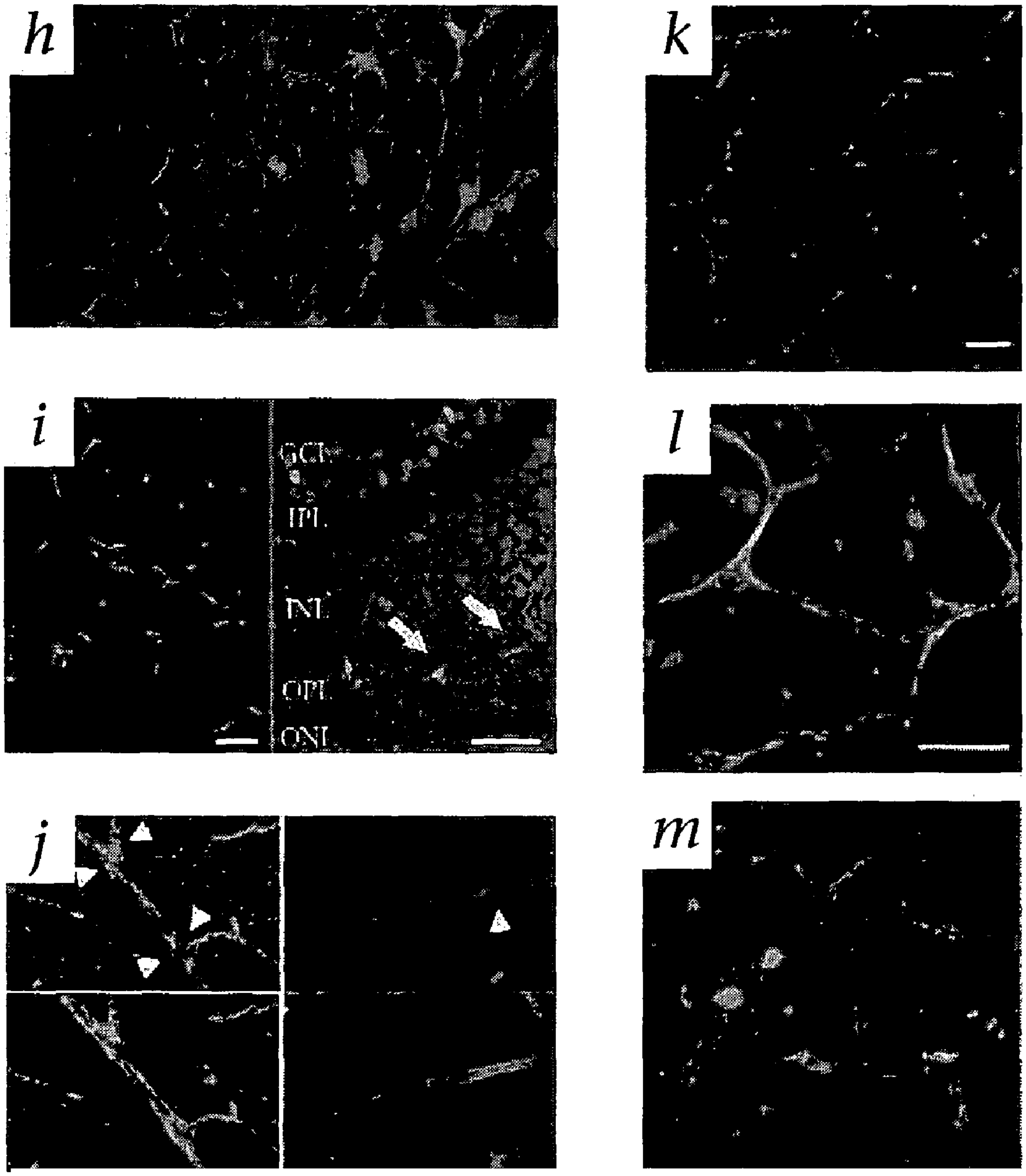

Intravitreally Injected HSC $Lin^-$ Cells Contain EPC That Target Astrocytes and Incorporate into Developing Retinal Vasculature To determine whether intravitreally injected $Lin^-$ HSC can target specific cell types of the retina, utilize the astrocytic template and participate in retinal angiogenesis, approximately $10^5$ cells from a $Lin^-$ HSC composition of the present invention or $Lin^+$ HSC cells (control, about $10^5$ cells) isolated from the bone marrow of adult (GFP or LacZ transgenic) mice were injected into postnatal day 2 (P2) mouse eyes. Four days after injection (P6), many cells from the $Lin^-$ HSC composition of the present invention, derived from GFP or LacZ transgenic mice were adherent to the retina and had the characteristic elongated appearance of endothelial cells (FIG. 2*a*). FIG. 2 illustrates engraftment of $Lin^-$ cells into developing mouse retina. As shown in FIG. 2*a*, the four days post-injection (P6) intravitreally injected eGFP+$Lin^-$ HSC attach and differentiate on the retina.

In many areas of the retinas, the GFP-expressing cells were arranged in a pattern conforming to underlying astrocytes and resembled blood vessels. These fluorescent cells were observed ahead of the endogenous, developing vascular network (FIG. 2*b*). Conversely, only a small number of $Lin^+$ HSC (FIG. 2*c*), or adult mouse mesenteric endothelial cells (FIG. 2*d*) attached to the retinal surface. In order to determine whether cells from an injected $Lin^-$ HSC composition could also attach to retinas with already established vessels, we injected a $Lin^-$ HSC composition into adult eyes. Interestingly, no cells were observed to attach to the retina or incorporate into established, normal retinal blood vessels (FIG. 2*e*). This indicates that the $Lin^-$ HSC compositions of the present invention do not disrupt a normally developed vasculature and will not initiate abnormal vascularization in normally developed retinas.

In order to determine the relationship between an injected $Lin^-$ HSC compositions of the present invention and retinal astrocytes, a transgenic mouse was used, which expressed glial fibrillary acidic protein (GFAP, a marker of astrocytes) and promoter-driven green fluorescent protein (GFP). Examination of retinas of these GFAP-GFP transgenic mice injected with $Lin^-$ HSC from eGFP transgenic mice demonstrated co-localization of the injected eGFP EPC and existing astrocytes (FIGS. 2*f–h*, arrows). Processes of eGFP+$Lin^-$ HSC were observed to conform to the underlying astrocytic network (arrows, FIG. 2*g*). Examination of these eyes demonstrated that the injected, labeled cells only attached to astrocytes; in P6 mouse retinas, where the retinal periphery does not yet have endogenous vessels, injected cells were observed adherent to astrocytes in these not yet vascularized areas. Surprisingly, injected, labeled cells were observed in the deeper layers of the retina at the precise location where normal retinal vessels will subsequently develop (FIG. 2*i*, arrows).

To determine whether injected $Lin^-$ HSC of the present invention are stably incorporated into the developing retinal vasculature, retinal vessels at several later time points were examined. As early as P9 (seven days after injection), $Lin^-$ HSC incorporated into $CD^+$ structures (FIG. 2*j*). By P16 (14 days after injection), the cells were already extensively incorporated into retinal vascular-like structures (FIG. 2*k*). When rhodamine-dextran was injected intravascularly (to identify functional retinal blood vessels) prior to sacrificing the animals, the majority of $Lin^-$ HSC were aligned with patent vessels (FIG. 21). Two patterns of labeled cell distribution were observed: (1) in one pattern, cells were interspersed along vessels in between unlabeled endothelial cells; and (2) the other pattern showed that vessels were composed entirely of labeled cells. Injected cells were also incorporated into vessels of the deep vascular plexus (FIG. 2*m*). While sporadic incorporation of $Lin^-$ HSC-derived EPC into neovasculature has been previously reported, this is the first report of vascular networks being entirely composed of these cells. This demonstrates that cells from a population of bone marrow-derived $Lin^-$ HSC of the present invention injected intravitreally can efficiently incorporate into any layer of the forming retinal vascular plexus.

Histological examination of non-retinal tissues (e.g., brain, liver, heart, lung, bone marrow) did not demonstrate the presence of any GFP positive cells when examined up to 5 or 10 days after intravitreal injection. This indicates that a sub-population of cells within the $Lin^-$ HSC fraction selectively target to retinal astrocytes and stably incorporate into developing retinal vasculature. Since these cells have many characteristics of endothelial cells (association with retinal astrocytes, elongate morphology, stable incorporation into patent vessels and not present in extravascular locations), these cells represent EPC present in the $Lin^-$ HSC population. The targeted astrocytes are of the same type observed in many of the hypoxic retinopathies; it is well known that glial cells are a prominent component of neovascular fronds observed in DR and other forms of retinal injury. Under conditions of reactive gliosis and ischemia-induced neovascularization, activated astrocytes proliferate, produce cytokines, and up-regulate GFAP, similar to that observed during neonatal retinal vascular template formation in many mammalian species including humans.

Figure 3:
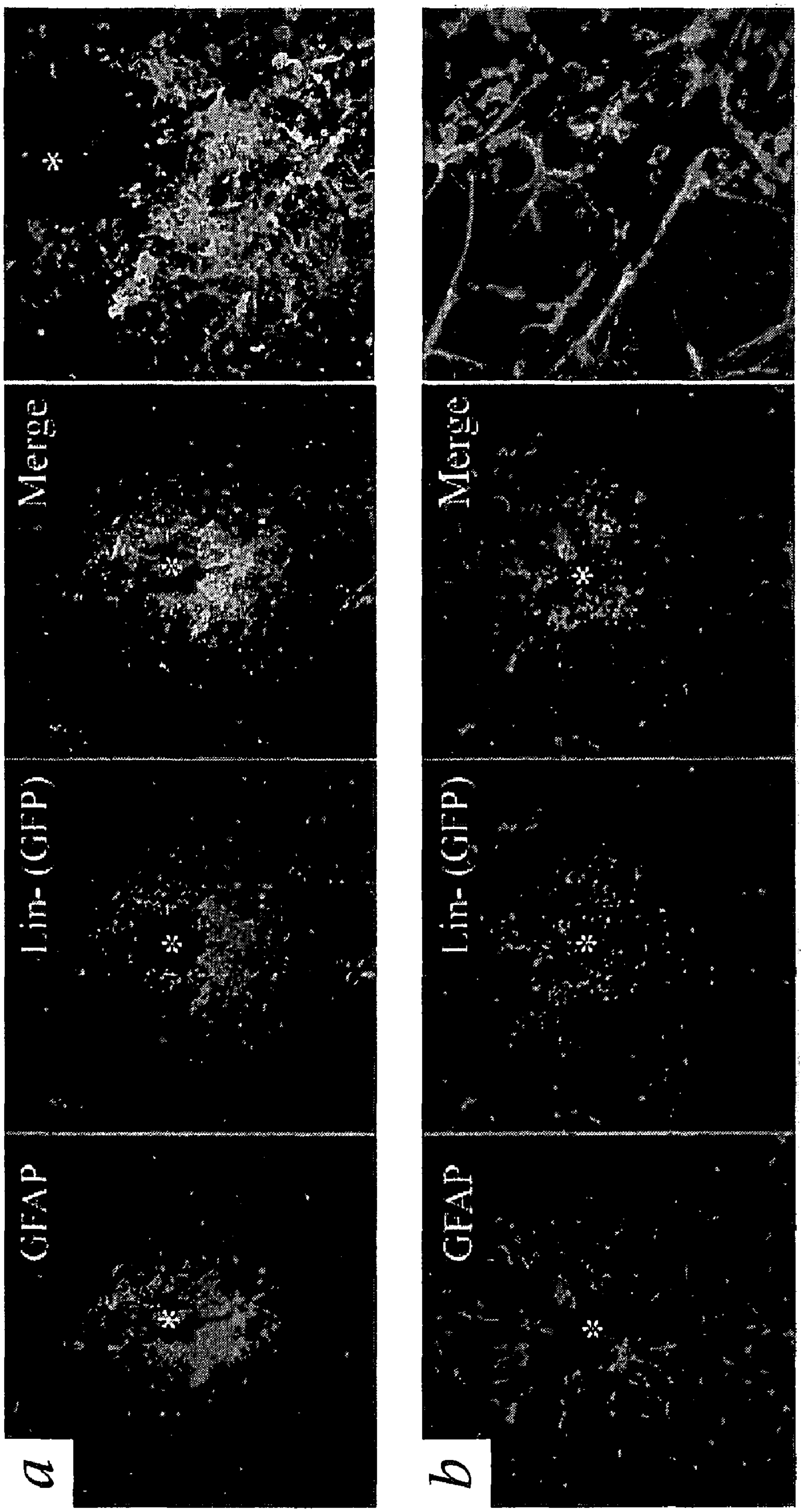
FIG. 3 (*a* and *b*) shows that $eGFP^+$ $Lin^-$ HSC cells home to the gliosis (indicated by GFAP expressing-astrocytes, far left image) induced by both laser (a) and mechanical (b) induced injury in the adult retina (asterisk indicates injured site). Far right images are a higher magnification, demonstrating the close association of the $Lin^-$ HSCs and astrocytes. Calibration bar=20 μM.

To test whether $Lin^-$ HSC compositions of the present invention will target activated astrocytes in adult mouse eyes as they do in neonatal eyes, $Lin^-$ HSC cells were injected into adult eyes with retinas injured by photo-coagulation (FIG. 3*a*) or needle tip (FIG. 3*b*). In both models, a population of cells with prominent GFAP staining was observed only around the injury site (FIGS. 3*a* and *b*). Cells from injected Lin$^-$ HSC compositions localized to the injury site and remained specifically associated with GFAP-positive astrocytes (FIGS. 3*a* and *b*). At these sites, Lin$^-$ HSC cells were also observed to migrate into the deeper layer of retina at a level similar to that observed during neonatal formation of the deep retinal vasculature (data not shown). Uninjured portions of retina contained no Lin$^-$ HSC cells, identical to that observed when Lin$^-$ HSC were injected into normal, uninjured adult retinas (FIG. 2*e*). These data indicate that Lin$^-$ HSC compositions can selectively target activated glial cells in injured adult retinas with gliosis as well as neonatal retinas undergoing vascularization.

Intravitreally Injected Lin$^-$ HSC Can Rescue and Stabilize Degenerating Vasculature Since intravitreally injected Lin$^-$ HSC compositions target astrocytes and incorporate into the normal retinal vasculature, these cells also stabilize degenerating vasculature in ischemic or degenerative retinal diseases associated with gliosis and vascular degeneration. The rd/rd mouse is a model for retinal degeneration that exhibits profound degeneration of photoreceptor and retinal vascular layers by one month after birth. The retinal vasculature in these mice develops normally until P16 at which time the deeper vascular plexus regresses; in most mice the deep and intermediate plexuses have nearly completely degenerated by P30.

Figure 4:
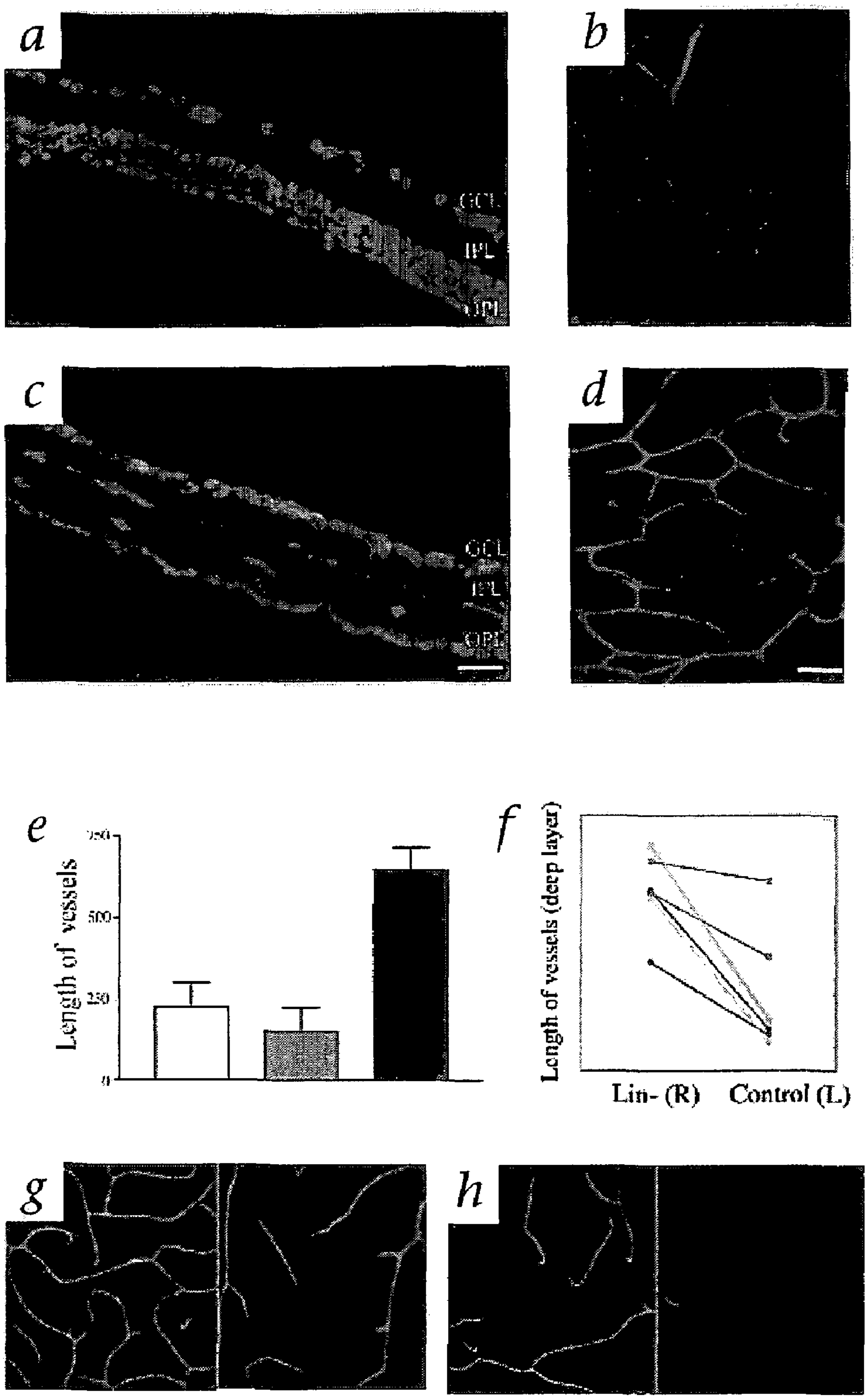
FIG. 4 shows that $Lin^-$ HSC cells rescue the vasculature of the retinal degeneration mouse. (a–d) Retinas at 27 days post-injection (P33) with collagen IV staining; (a) and (b), retinas injected with $Lin^+$ HSC cells (Balb/c) showed no difference in vasculature from normal FVB mice; (c) and (d) retinas injected with $Lin^-$ HSCs (Balb/c) exhibited a rich vascular network analogous to a wild-type mouse; (a) and (c), frozen sections of whole retina (top is vitreal side, bottom is scleral side) with DAPI staining; (b) and (d), deep plexus of retinal whole amount; (e) bar graph illustrating the increase in vascularity of the deep vascular plexus formed in the $Lin^-$ HSC cell-injected retinas (n=6). The extent of deep retinal vascularization was quantified by calculating the total length of vessels within each image. Average total length of vessels/high power field (in microns) for $Lin^-$ HSC, $Lin^+$ HSC or control retinas were compared. (f) Comparison of the length of deep vascular plexus after injection with $Lin^-$ HSC (R, right eye) or $Lin^+$ HSC (L, left eye) cells from rd/rd mouse. The results of six independent mice are shown (each color represents each mouse). (g) and (h) $Lin^-$ HSC cells also (Balb/c) rescued the rd/rd vasculature when injected into P15 eyes. The intermediate and deep vascular plexus of $Lin^-$ HSC (G) or $Lin^+$ HSC (H) cell injected retinas (one month after injection) are shown.

To determine whether HSC can rescue the regressing vessels, Lin$^+$ or Lin$^-$ HSC (from Balb/c mice) were injected into rd/rd mice intravitreally at P6. By P33, after injection with Lin$^+$ cells, vessels of the deepest retinal layer were nearly completely absent (FIGS. 4*a* and *b*). In contrast, most Lin$^-$ HSC-injected retinas by P33 had a nearly normal retinal vasculature with three parallel, well-formed vascular layers (FIGS. 4*a* and 4*d*). Quantification of this effect demonstrated that the average length of vessels in the deep vascular plexus of Lin$^-$ injected rd/rd eyes was nearly three times greater than untreated or Lin$^+$ cell-treated eyes (FIG. 4*e*). Surprisingly, injection of a Lin$^-$ HSC composition derived from rd/rd adult mouse (FVB/N) bone marrow also rescued degenerating rd/rd neonatal mouse retinal vasculature (FIG. 4*f*). Degeneration of the vasculature in rd/rd mouse eyes in observed as early as 2–3 weeks post-natally. Injection of Lin$^-$ HSC as late as P15 also resulted in partial stabilization of the degenerating vasculature in the rd/rd mice for at least one month (FIGS. 4*g* and 4*h*).

Figure 5:
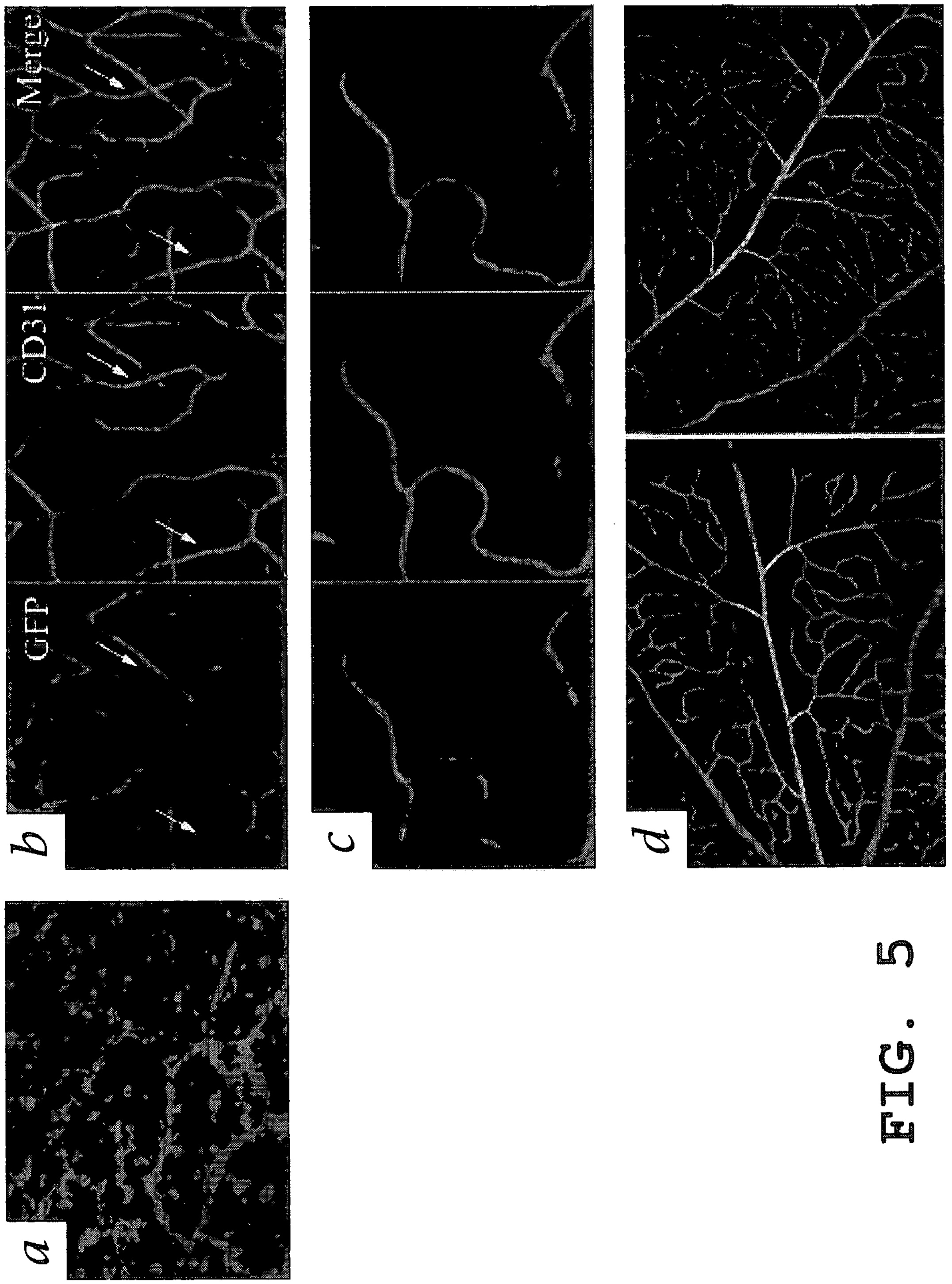
FIG. 5 depicts photomicrographs of mouse retinal tissue: (a) deep layer of retinal whole mount (rd/rd mouse), five days post-injection (P11) with $eGFP^+$ $Lin^-$ HSCs (green). (b) and (c) P60 retinal vasculature of Tie-2-GFP (rd/rd) mice that received Balb/c $Lin^-$ cells (A) or $Lin^+$ HSC cell (B) injection at P6. The vasculature was stained with CD31 antibody (red) and only endogenous endothelial cells present green color. Arrows indicate the vessels stained with CD31 but not with GFP. (d) α-SMA staining of $Lin^-$ HSC injected and control retina.

A Lin$^-$ HSC composition injected into younger (e.g., P2) rd/rd mice also incorporated into the developing superficial vasculature. By P11, these cells were observed to migrate to the level of the deep vascular plexus and form a pattern identical to that observed in the wild type outer retinal vascular layer (FIG. 5*a*). In order to more clearly describe the manner in which cells from injected Lin$^-$ HSC compositions incorporate into, and stabilize, degenerating retinal vasculature in the rd/rd mice, a Lin$^-$ HSC composition derived from Balb/c mice was injected into Tie-2-GFP FVB mouse eyes. The FVB mice have the rd/rd genotype and because they express the fusion protein Tie-2-GFP, all endogenous blood vessels are fluorescent.

When non-labeled cells from a Lin$^-$ HSC composition are injected into neonatal Tie-2-GFP FVB eyes and are subsequently incorporated into the developing vasculature, there should be non-labeled gaps in the endogenous, Tie-2-GFP labeled vessels that correspond to the incorporated, non-labeled Lin$^-$ HSC that were injected. Subsequent staining with another vascular marker (e.g., CD-31) then delineates the entire vessel, permitting determination as to whether non-endogenous endothelial cells are part of the vasculature. Two months after injection, CD31-positive, Tie-2-GFP negative, vessels were observed in the retinas of eyes injected with the Lin$^-$ HSC composition (FIG. 5*b*). Interestingly, the majority of rescued vessels contained Tie-2-GFP positive cells (FIG. 5*c*). The distribution of pericytes, as determined by staining for smooth muscle actin, was not changed by Lin$^-$ HSC injection, regardless of whether there was vascular rescue (FIG. 5*d*). These data clearly demonstrate that intravitreally injected Lin$^-$ HSC compositions of the present invention migrate into the retina, participate in the formation of normal retinal blood vessels, and stabilize endogenous degenerating vasculature in a genetically defective mouse.

Inhibition of Retinal Angiogenesis by Transfected Cells from Lin$^-$ Hsc

Figure 6:
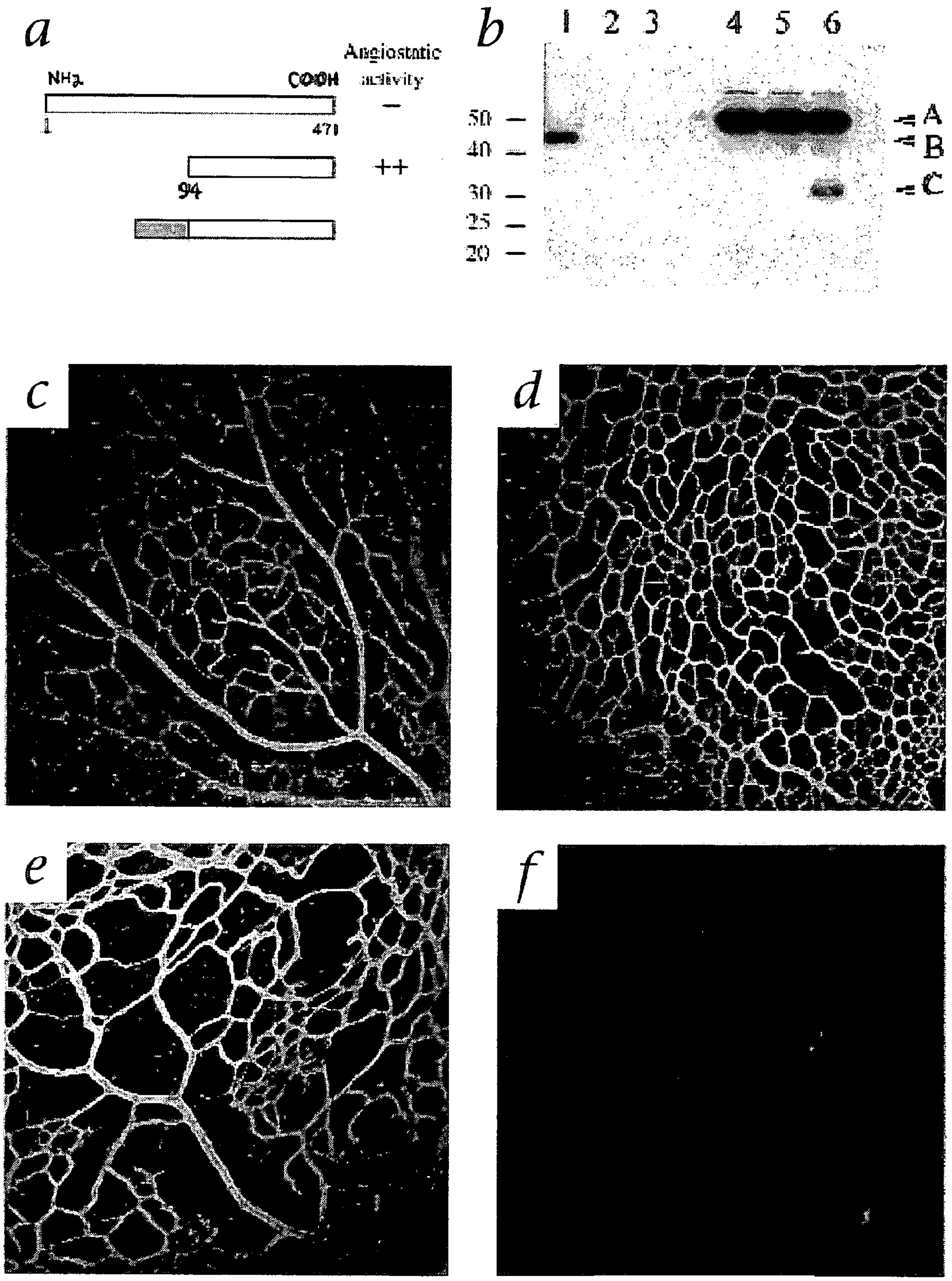
FIG. 6 shows that T2-TrpRS-transfected $Lin^-$ HSCs inhibit the development of mouse retinal vasculature. (a) Schematic representation of human TrpRS, T2-TrpRS and T2-TrpRS with an Igk signal sequence at the amino terminus. (b) T2-TrpRS transfected $Lin^-$ cells injected retinas express T2-TrpRS protein in vivo. 1, Recombinant T2-TrpRS produced in *E. coli;* 2, Recombinant T2-TrpRS produced in *E. coli;* 3, Recombinant T2-TrpRS produced in *E. coli;* 4, control retina; 5, $Lin^-$ HSC+ pSecTag2A (vector only) injected retina; 6, $Lin^-$ HSC+ pKLe 135 (Igk-T2-TrpRS in pSecTag) injected retina. (a); endogenous TrpRS b; recombinant T2-TrpRS c; T2-TrpRS of $Lin^-$ HSC injected retina). (c–f) Representative primary (superficial) and secondary (deep) plexuses of injected retinas, seven days post-injection; (c) and (d), Eyes injected with empty plasmid-transfected $Lin^-$ HSC developed normally; (e) and (f), the majority of T2-TrpRS-transfected $Lin^-$ HSC injected eyes exhibited inhibition of deep plexus; (c) and (e), primary (superficial) plexus; (d) and (f), secondary (deep) plexus). Faint outline of vessels observed in F are "bleed-through" images of primary network vessels shown in (e).

The majority of retinal vascular diseases involve abnormal vascular proliferation rather than degeneration. Transgenic cells targeted to astrocytes can be used to deliver an anti-angiogenic protein and inhibit angiogenesis. Cells from Lin$^-$ HSC compositions were transfected with T2-tryptophanyl-tRNA synthetase (T2-TrpRS). T2-TrpRS is a 43 kD fragment of TrpRS that potently inhibits retinal angiogenesis (FIG. 6*a*). On P12, retinas of eyes injected with a control plasmid-transfected Lin$^-$ HSC composition (no T2-TrpRS gene) on P2 had normal primary (FIG. 6*c*) and secondary (FIG. 6*d*) retinal vascular plexuses. When the T2-TrpRS transfected Lin$^-$ HSC composition of the present invention was injected into P2 eyes and evaluated 10 days later, the primary network had significant abnormalities (FIG. 6*e*) and formation of the deep retinal vasculature was nearly completely inhibited (FIG. 6*f*). The few vessels observed in these eyes were markedly attenuated with large gaps between vessels. The extent of inhibition by T2-TrpRS-secreting Lin$^-$ HSC cells is detailed in Table 2.

T2-TrpRS is produced and secreted by cells in the Lin$^-$ HSC composition in vitro and after injection of these transfected cells into the vitreous, a 30 kD fragment of T2-TrpRS in the retina (FIG. 6*b*) was observed. This 30 kD fragment was specifically observed only in retinas injected with transfected Lin$^-$ HSC of the present invention and this decrease in apparent molecular weight compared to the recombinant or in vitro-synthesized protein may be due to processing or degradation of the T2-TrpRS in vivo. These data indicate that Lin$^-$ HSC compositions can be used to deliver functionally active genes, such as genes expressing angiostatic molecules, to the retinal vasculature by targeting to activated astrocytes. While it is possible that the observed angiostatic effect is due to cell-mediated activity this is very unlikely since eyes treated with identical, but non-T2-transfected Lin$^-$ HSC compositions had normal retinal vasculature.

TABLE 2

Vascular Inhibition by T2-TrpRS-secreting Lin$^-$ HSC Cells

| | Primary Plexus | | Deep Plexus | | |
|---|---|---|---|---|---|
| | Inhibited | Normal | Complete | Partial | Normal |
| TsTrpRs (15 eyes) | 60% (9 eyes) | 40% (6 eyes) | 33.3% (5 eyes) | 60% (9 eyes) | 6.7% (1 eye) |
| Control (13 eyes) | 0% (0 eyes) | 100% (13 eyes) | 0% (0 eyes) | 38.5% (5 eyes) | 61.5% (8 eyes) |

Intravitreally injected Lin$^-$ HSC compositions localize to retinal astrocytes, incorporate into vessels, and can be useful in treating many retinal diseases. While most cells from injected HSC compositions adhere to the astrocytic template, small numbers migrate deep into the retina, homing to regions where the deep vascular network will subsequently develop. Even though no GFAP-positive astrocytes were observed in this area prior to 42 days postnatally, this does not rule out the possibility that GFAP-negative glial cells are already present to provide a signal for Lin⁻ HSC localization. Previous studies have shown that many diseases are associated with reactive gliosis. In DR, in particular, glial cells and their extracellular matrix are associated with pathological angiogenesis.

Since cells from injected Lin⁻ HSC compositions specifically attached to GFAP-expressing glial cells, regardless of the type of injury, Lin⁻ HSC compositions of the present invention can be used to target pre-angiogenic lesions in the retina. For example, in the ischemic retinopathies such as diabetes, neovascularization is a response to hypoxia. By targeting Lin⁻ HSC compositions to sites of pathological neovascularization, developing neovasculature can be stabilized preventing abnormalities of neovasculature such as hemorrhage or edema (the causes of vision loss associated with DR) and can potentially alleviate the hypoxia that originally stimulated the neovascularization. Abnormal blood vessels can be restored to normal condition. Furthermore, angiostatic proteins, such as T2-TrpRS can be delivered to sites of pathological angiogenesis by using transfected Lin⁻ HSC compositions and laser-induced activation of astrocytes. Since laser photocoagulation is a commonly used in clinical ophthalmology, this approach has application for many retinal diseases. While such cell-based approaches have been explored in cancer therapy, their use for eye diseases is more advantageous since intraocular injection makes it possible to deliver large numbers of cells directly to the site of disease.

Neurotrophic and Vasculotrophic Rescue by Lin⁻HSC

MACS was used to separate Lin⁻ HSC from bone marrow of enhanced green fluorescent protein (eGFP), C3H (rd/rd), FVB (rd/rd) mice as described above. Lin⁻ HSC containing EPC from these mice were injected intravitreally into P6 C3H or FVB mouse eyes. The retinas were collected at various time points (1 month, 2 months, and 6 months) after injection. The vasculature was analyzed by scanning laser confocal microscope after staining with antibodies to CD31 and retinal histology after nuclear staining with DAPI. Microarray gene expression analysis of mRNA from retinas at varying time points was also used to identify genes potentially involved in the effect.

Eyes of rd/rd mice had profound degeneration of both neurosensory retina and retinal vasculature by P21. Eyes of rd/rd mice treated with Lin⁻ HSC on P6 maintained a normal retinal vasculature for as long as 6 months; both deep and intermediate layers were significantly improved when compared to the controls at all timepoints (1M, 2M, and 6M) (see FIG. 12). In addition, we observed that retinas treated with Lin⁻HSC were also thicker (1M; 1.2-fold, 2M; 1.3-fold, 6M; 1.4-fold) and had greater numbers of cells in the outer nuclear layer (1M; 2.2-fold, 2M; 3.7-fold, 6M; 5.7-fold) relative to eyes treated with Lin⁺ HSC as a control. Large scale genomic analysis of "rescued" (e.g., Lin⁻HSC) compared to control (untreated or non-Lin⁻ treated) rd/rd retinas demonstrated a significant up-regulation of genes encoding sHSPs (small heat shock proteins) and specific growth factors that correlated with vascular and neural rescue, including factors shown in Table 3.

The bone marrow derived Lin⁻ HSC of the present invention significantly and reproducibly induce maintenance of a normal vasculature and dramatically increase photoreceptor and other neuronal cell layers in the rd/rd mouse. This neurotrophic rescue effect is correlated with significant up-regulation of small heat shock proteins and growth factors and, thus, provides insights into therapeutic approaches to currently untreatable retinal degenerative disorders.

TABLE 3

Genes Upregulated in Lin⁻ HSC Injected Mouse Retinas

| Common Name | Lin (−) | CD31 (−) | Control rd mice | Genbank # | Comments |
|---|---|---|---|---|---|
| Tgtp | 11.855 | 0.526 | 0.664 | L38444 | T-cell-specific protein |
| H-2D4(q) | 7.091 | 0.916 | 0.694 | X52914 | transplantation antigen |
| H2-K2; H-2K2 | 4.507 | 0.705 | 0.547 | M27134 | cell surface glycoprotein |
| Lzp-s | 6.514 | 0.648 | 0.987 | X51547 | lysozyme; lysozyme P |
| Kcnj5 | 4.501 | 0.855 | 0.722 | U33631 | G-protein gated K+ channel |
| EST | 2.905 | 1.000 | 0.750 | AA087373 | EST |
| Scya8 | 5.186 | 0.470 | 0.996 | AB023418 | MCP-2 precursor |
| Ly6a | 4.020 | 0.962 | 0.792 | X04653 | Ly-6 alloantigen |
| Anxa1 | 2.490 | 0.599 | 0.510 | AV003419 | EST |
| Pip5k1c | 3.405 | 0.944 | 0.782 | AB006916 | phosphatidylinositolkinase |
| EST | 3.999 | 0.502 | 0.975 | AU042276 | EST |
| MAD | 3.763 | 0.560 | 0.892 | X83106 | MAX dimerization protein |
| Cxadr | 3.977 | 0.814 | 1.000 | U90715 | CAR |
| Isg15 | 2.218 | 0.642 | 0.449 | X56602 | interferon inducible protein |
| EST | 3.512 | 0.901 | 0.978 | AA790936 | EST |
| Tm4sf1 | 3.022 | 0.493 | 0.697 | AV087000 | EST |
| IgG VH-II | 2.644 | 0.948 | 0.909 | X02463 | Ig heavy chain; variable region |
| Yy1 | 2.967 | 0.854 | 0.874 | M74590 | delta-transcription factor |
| EST | 2.952 | 0.869 | 0.822 | AA739246 | EST |
| EST | 2.575 | 0.486 | 0.650 | AW046243 | EST |
| Psmb9 | 3.288 | 0.492 | 0.975 | D44456 | polypeptide complex subunit 2 |
| EST | 2.195 | 0.873 | 0.904 | AV172782 | EST |
| H2-Aa | 2.627 | 0.878 | 0.940 | X52643 | I-E alpha NON, MHC |
| EST | 2.697 | 0.791 | 0.869 | AV076889 | EST |

TABLE 3-continued

| Genes Upregulated in $Lin^-$ HSC Injected Mouse Retinas | | | | | |
|---|---|---|---|---|---|
| Common Name | Lin (–) | CD31 (–) | Control rd mice | Genbank # | Comments |
| Crystallin genes | | | | | |
| Crybb2 | 8.726 | 0.552 | 0.831 | M60559 | beta-B2-crystallin |
| Cryaa | 3.995 | 0.567 | 1.000 | J00376 | alpha-A-crystallin |
| CrygD | 2.090 | 0.740 | 0.972 | AJ224342 | gamma-D-crystallin |
| Crybal | 6.520 | 0.930 | 0.603 | AJ239052 | beta-A3/A1-crystallin |
| Crygs | 2.892 | 0.971 | 0.854 | AF032995 | gamma-S-crystallin |
| CrygC | 5.067 | 1.000 | 0.826 | Z22574 | gamma-C-crystallin |
| CrygF | 1.942 | 0.999 | 0.688 | AJ224343 | gamma-F-crystallin |

Discussion.

Markers for lineage-committed hematopoietic cells were used to negatively select a population of bone marrow-derived $Lin^-$ HSC containing EPC. While the sub-population of bone marrow-derived $Lin^-$ HSC that can serve as EPC is not characterized by commonly used cell surface markers, the behavior of these cells in developing or injured retinal vasculature is entirely different than that observed for $Lin^+$ or adult endothelial cell populations. Further subfractionation of HSC using markers such as Sca-1, indicated that $Lin^-Sca^+$ cells did not show any substantial difference from the use of $Lin^-$ HSC cells alone. These cells selectively target to sites of retinal angiogenesis and participate in the formation of patent blood vessels.

Inherited retinal degenerative diseases are often accompanied by loss of retinal vasculature. Effective treatment of such diseases requires restoration of function as well as maintenance of complex tissue architecture. While several recent studies have explored the use of cell-based delivery of trophic factors or stem cells themselves, some combination of both may be necessary. For example, use of growth factor therapy to treat retinal degenerative disease resulted in unregulated overgrowth of blood vessels resulting in severe disruption of the normal retinal tissue architecture. The use of neural or retinal stem cells to treat retinal degenerative disease may reconstitute neuronal function, but a functional vasculature will also be necessary to maintain retinal functional integrity. Incorporation of cells from a $Lin^-$ HSC composition of the present invention into the retinal vessels of rd/rd mice stabilized the degenerative vasculature without disrupting retinal structure. This rescue effect was also observed when the cells were injected into P15 rd/rd mice. Since vascular degeneration begins on P16 in rd/rd mice, this observation expands the therapeutic window for effective $Lin^-$ HSC treatment. Retinal neurons and photoreceptors are preserved and visual function is maintained in eyes injected with the $Lin^-$ HSC of the present invention.

$Lin^-$ HSC compositions of the present invention contain a population of EPC that can promote angiogenesis by targeting reactive astrocytes and incorporate into an established template without disrupting retinal structure. The $Lin^-$ HSC of the present invention also provide a surprising long-term neurotrophic rescue effect in eyes suffering from retinal degeneration. In addition, genetically modified, autologous $Lin^-$ HSC compositions containing EPC can be transplanted into ischemic or abnormally vascularized eyes and can stably incorporate into new vessels and continuously deliver therapeutic molecules locally for prolonged periods of time. Such local delivery of genes that express pharmacological agents in physiologically meaningful doses represents a new paradigm for treating currently untreatable ocular diseases.

We claim:

1. An isolated and transfected lineage negative hematopoietic stem cell population containing endothelial progenitor cells in which at least about 50% of all cells in said stem cell population express cell markers for CD31 and c-kit, and not more than about 1% of all cells in said stem cell population express the Tie-2 marker, and where the cells of said stem cell population are transfected with a DNA encoding an anti-angiogenic peptide, an anti-angiogenic protein or an anti-angiogenic protein fragment.

2. The transfected stem cell population of claim 1 wherein the anti-angiogenic protein fragment is an anti-angiogenic protein fragment of tryptophanyl-tRNA synthetase (TrpRS).

3. The transfected stem cell population of claim 2 wherein the anti-angiogenic protein fragment of TrpRS is T2-TrpRS.

* * * * *

SEQUENCE LISTING

<160> NUMBER OF SEQ ID NOS: 2

<210> SEQ ID NO 1
<211> LENGTH: 4742
<212> TYPE: DNA
<213> ORGANISM: Artificial Sequence
<220> FEATURE:
<223> OTHER INFORMATION: DNA encoding His-tagged human T2-TrpRS

<400> SEQUENCE: 1
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300

-continued

```
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg agacaataac cctgataaat gcttcaataa tattgaaaaa ggaagagtat    600
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca gaccccgtag aaaagatcaa   1620
aggatcttct tgagatcctt tttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
```

-continued

```
catcagcgtg gtcgtgaagc gattcacaga tgtctgcctg ttcatccgcg tccagctcgt   2760

tgagtttctc cagaagcgtt aatgtctggc ttctgataaa gcgggccatg ttaagggcgg   2820

tttttcctg tttggtcact gatgcctccg tgtaaggggg atttctgttc atgggggtaa   2880

tgataccgat gaaacgagag aggatgctca cgatacgggt tactgatgat gaacatgccc   2940

ggttactgga acgttgtgag ggtaaacaac tggcggtatg gatgcggcgg gaccagagaa   3000

aaatcactca gggtcaatgc cagcgcttcg ttaatacaga tgtaggtgtt ccacagggta   3060

gccagcagca tcctgcgatg cagatccgga acataatggt gcagggcgct gacttccgcg   3120

tttccagact ttacgaaaca cggaaaccga agaccattca tgttgttgct caggtcgcag   3180

acgttttgca gcagcagtcg cttcacgttc gctcgcgtat cggtgattca ttctgctaac   3240

cagtaaggca accccgccag cctagccggg tcctcaacga caggagcacg atcatgcgca   3300

cccgtggcca ggacccaacg ctgcccgaga tctcgatccc gcgaaattaa tacgactcac   3360

tatagggaga ccacaacggt ttccctctag aaataatttt gtttaacttt aagaaggaga   3420

tatacatatg agtgcaaaag gcatagacta cgataagctc attgttcggt ttggaagtag   3480

taaaattgac aaagagctaa taaaccgaat agagagagcc accggccaaa gaccacacca   3540

cttcctgcgc agaggcatct tcttctcaca cagagatatg aatcaggttc ttgatgccta   3600

tgaaaataag aagccatttt atctgtacac gggccggggc ccctcttctg aagcaatgca   3660

tgtaggtcac ctcattccat ttattttcac aaagtggctc caggatgtat ttaacgtgcc   3720

cttggtcatc cagatgacgg atgacgagaa gtatctgtgg aaggacctga ccctggacca   3780

ggcctatggc gatgctgttg agaatgccaa ggacatcatc gcctgtggct ttgacatcaa   3840

caagactttc atattctctg acctggacta catggggatg agctcaggtt tctacaaaaa   3900

tgtggtgaag attcaaaagc atgttacctt caaccaagtg aaaggcattt tcggcttcac   3960

tgacagcgac tgcattggga agatcagttt tcctgccatc caggctgctc cctccttcag   4020

caactcattc ccacagatct tccgagacag gacggatatc cagtgcctta tcccatgtgc   4080

cattgaccag gatccttact ttagaatgac aagggacgtc gcccccagga tcggctatcc   4140

taaaccagcc ctgttgcact ccaccttctt cccagccctg cagggcgccc agaccaaaat   4200

gagtgccagc gacccaaact cctccatctt cctcaccgac acggccaagc agatcaaaac   4260

caaggtcaat aagcatgcgt tttctggagg gagagacacc atcgaggagc acaggcagtt   4320

tgggggcaac tgtgatgtgg acgtgtcttt catgtacctg accttcttcc tcgaggacga   4380

cgacaagctc gagcagatca ggaaggatta caccagcgga gccatgctca ccggtgagct   4440

caagaaggca ctcatagagg ttctgcagcc cttgatcgca gagcaccagg cccggcgcaa   4500

ggaggtcacg gatgagatag tgaaagagtt catgactccc cggaagctgt ccttcgactt   4560

tcagaagctt gcggccgcac tcgagcacca ccaccaccac cactgagatc cggctgctaa   4620

caaagcccga aaggaagctg agttggctgc tgccaccgct gagcaataac tagcataacc   4680

ccttggggcc tctaaacggg tcttgagggg ttttttgctg aaaggaggaa ctatatccgg   4740

at                                                                  4742
```

<210> SEQ ID NO 2
<211> LENGTH: 392
<212> TYPE: PRT
<213> ORGANISM: Artificial Sequence
<220> FEATURE:
<223> OTHER INFORMATION: His-tagged human T2-TrpRS -continued

<400> SEQUENCE: 2

```
Met Ser Ala Lys Gly Ile Asp Tyr Asp Lys Leu Ile Val Arg Phe Gly
 1               5                  10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
        35                  40                  45

Arg Asp Met Asn Gln Val Leu Asp Ala Tyr Glu Asn Lys Lys Pro Phe
    50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Gly Asp Ala Val Glu Asn Ala Lys
        115                 120                 125

Asp Ile Ile Ala Cys Gly Phe Asp Ile Asn Lys Thr Phe Ile Phe Ser
    130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe
        355                 360                 365

Met Thr Pro Arg Lys Leu Ser Phe Asp Phe Gln Lys Leu Ala Ala Ala
    370                 375                 380

Leu Glu His His His His His His
385                 390
```